(12) United States Patent
Chu

(10) Patent No.: US 9,888,917 B2
(45) Date of Patent: Feb. 13, 2018

(54) MEDICAL DEVICE AND METHOD FOR INJECTING A FLUID

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 431 days.

(21) Appl. No.: 14/271,996

(22) Filed: May 7, 2014

(65) Prior Publication Data

US 2014/0371706 A1  Dec. 18, 2014

Related U.S. Application Data

(60) Provisional application No. 61/835,910, filed on Jun. 17, 2013.

(51) Int. Cl.
*A61M 29/02* (2006.01)
*A61B 17/06* (2006.01)
*A61F 2/00* (2006.01)
*A61B 17/00* (2006.01)

(52) U.S. Cl.
CPC .. *A61B 17/06109* (2013.01); *A61B 17/00491* (2013.01); *A61B 2017/00805* (2013.01); *A61B 2017/00893* (2013.01); *A61B 2017/06023* (2013.01); *A61F 2/0063* (2013.01)

(58) Field of Classification Search
CPC ........ A61B 17/06109; A61B 17/00491; A61B 2017/00893; A61B 2017/06023; A61B 2017/00805; A61F 2/0063
See application file for complete search history.

(56) References Cited

U.S. PATENT DOCUMENTS

2005/0131393 A1* 6/2005 Chu ................. A61B 17/00234 606/1
2005/0256366 A1* 11/2005 Chu ................. A61B 17/06066 600/30
2009/0171140 A1* 7/2009 Chu ................... A61B 17/0482 600/37

* cited by examiner

*Primary Examiner* — Kevin C Sirmons
*Assistant Examiner* — Amber Stiles
(74) *Attorney, Agent, or Firm* — Brake Hughes Bellermann LLP

(57) ABSTRACT

In one general aspect, a medical device can include an implant having a medial portion and a distal portion. The medical device can include a delivery member including a dilator having a distal portion, and a tube coupled to the dilator. The tube can define a lumen in fluid communication with an opening in the tube. The opening can be disposed between the distal portion of the implant and the distal portion of the dilator of the delivery member. The medical device can include a sleeve having a lumen. The distal portion of the implant and at least a portion of the delivery member can be disposed within the lumen portion of the sleeve.

15 Claims, 14 Drawing Sheets

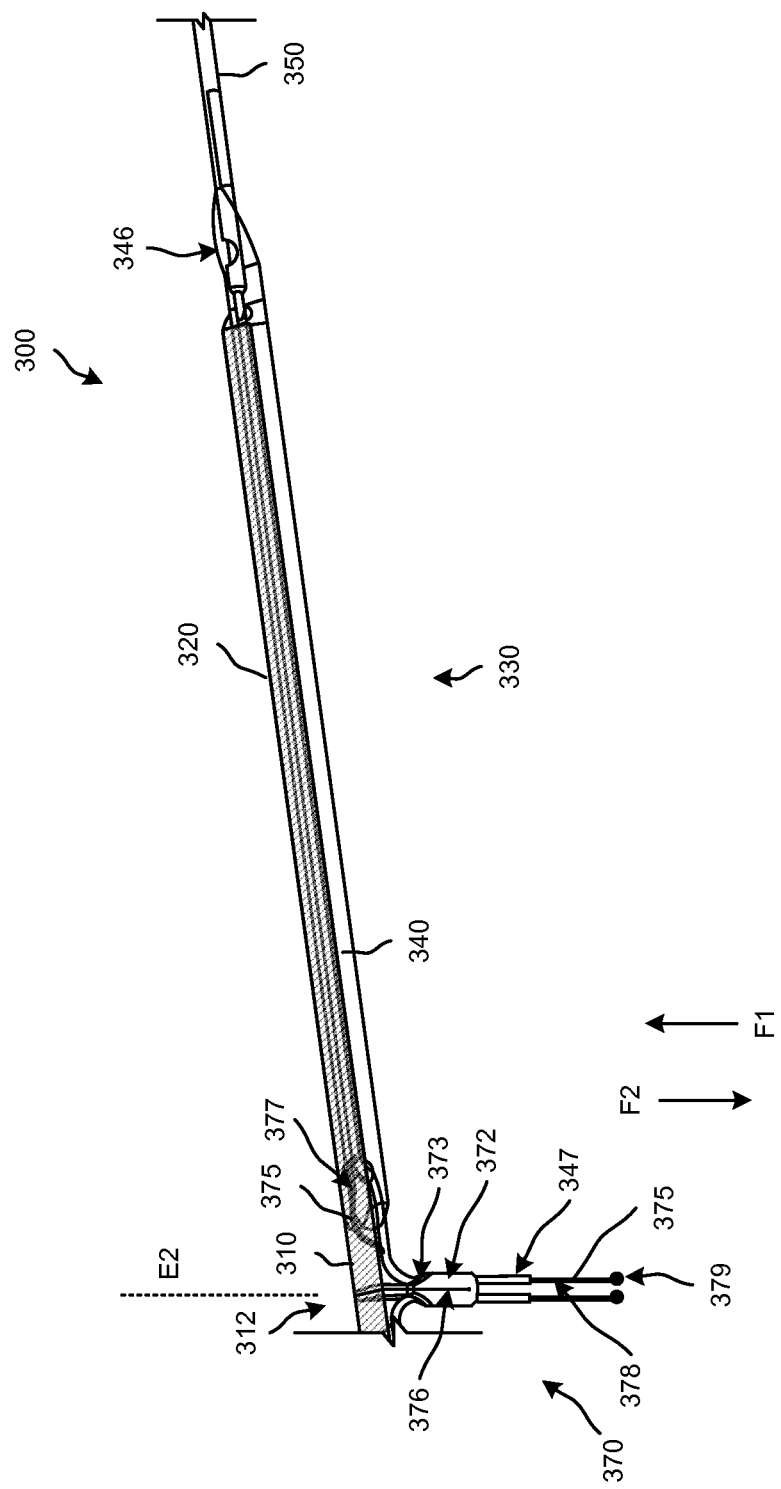

MEDICAL DEVICE AND METHOD FOR INJECTING A FLUID

CROSS-REFERENCE TO RELATED APPLICATION

This application is a Nonprovisional of, and claims priority to, U.S. Patent Application No. 61/835,910, filed on Jun. 17, 2013, entitled "MEDICAL DEVICE AND METHOD FOR INJECTING A FLUID", which is incorporated by reference herein in its entirety.

TECHNICAL FIELD

This disclosure generally relates to medical devices and procedures, and particularly to devices and methods for delivery of implants and medication in a body of a patient.

BACKGROUND

Pelvic organ prolapse is an abnormal descent or herniation of pelvic organs. A prolapse may occur when muscles and/or tissues in the pelvic region become weak and can no longer properly maintain the pelvic organs in place. This decrease in structural integrity of anatomical tissues may have significant medical consequences, which in turn could influence the biological functions of the tissues.

Treatment for symptoms of the pelvic organ prolapse can include changes in diet, weight control, and lifestyle. Treatment may also include surgery, medication, and use of grafts or implants to support the pelvic organs. For example, an implant can be placed in a patient to provide support for the weakened or damaged tissue. The implant can replicate the natural position and structure of, or otherwise, provide support to the tissue and thereby help in decreasing or eliminating impairment of biological functions resulting from tissue weakening or damage.

These surgical methods may use a delivery device for assisting delivery of the implant to the anatomical tissue inside the patient's body. A medication may be applied through the delivery device simultaneously during the introduction of the implant inside the body of the patient. The medication may be beneficial to a patient during placement of the implant to, for example, manage post-surgical pain, or prevent infection or excess bleeding and the like. There may generally be a requirement of maintaining a tactile feedback with a needle of the delivery device during implant placement to prevent injury to any bodily tissues such as a bladder. Therefore, the injection of the medication along with delivery of the implant may require alternative and frequent steps of stopping, aspirating and then injecting along the needle track while maintaining the tactile feedback. This may complicate the method of implant and medication delivery, and also may be time consuming. Thus, there is a need for a device and a surgical procedure that facilitates delivery and placement of implants, and facilitates delivery of medication or any other types of fluid inside a body during a medical procedure.

SUMMARY

In one general aspect, a medical device can include an implant having a medial portion and a distal portion. The medical device can include a delivery member including a dilator having a distal portion, and a tube coupled to the dilator. The tube can define a lumen in fluid communication with an opening in the tube. The opening can be disposed between the distal portion of the implant and the distal portion of the dilator of the delivery member. The medical device can include a sleeve having a lumen. The distal portion of the implant and at least a portion of the delivery member can be disposed within the lumen portion of the sleeve.

BRIEF DESCRIPTION OF THE FIGURES

FIGS. 3A through 3D are various views of a medical device in accordance with an implementation.

DETAILED DESCRIPTION

In general, this disclosure is directed to systems, methods, and devices for treating incontinence, such as urinary incontinence. However, this disclosure may be employed for other treatment purposes such as pelvic organ prolapse or other pelvic disorders. As described below in various illustrative implementations, this disclosure provides systems, methods, and devices employing a medical device configured to deliver or place an implant within a body of a patient to support pelvic organs and deliver a fluid such as a medication inside the body such as to an implant site for the treatment of incontinence or other pelvic disorders.

The term patient may be used hereafter for a person who benefits from the medical device or the methods disclosed herein. For example, the patient may be a person whose body is operated with the use of the medical device disclosed herein in a medical procedure (e.g., a surgical treatment). For example, in some implementations, the patient may be a human female, human male, or any other mammal.

In some implementations, the terms proximal and distal can be used to describe portions of various devices or components with respect to a point of reference. In some implementations, the point of reference can be from a perspective of an operator where the term proximal can refer to an area, location, or component that is relatively close to the operator, and the term distal can refer to an area, location, or component that is relatively far from the operator. In some implementations, the operator may be a surgeon, a physician, a nurse, a doctor, a technician, and so forth. The operator may perform one or more procedures including delivery and placement of implants into a body of a patient.

Figure 1:
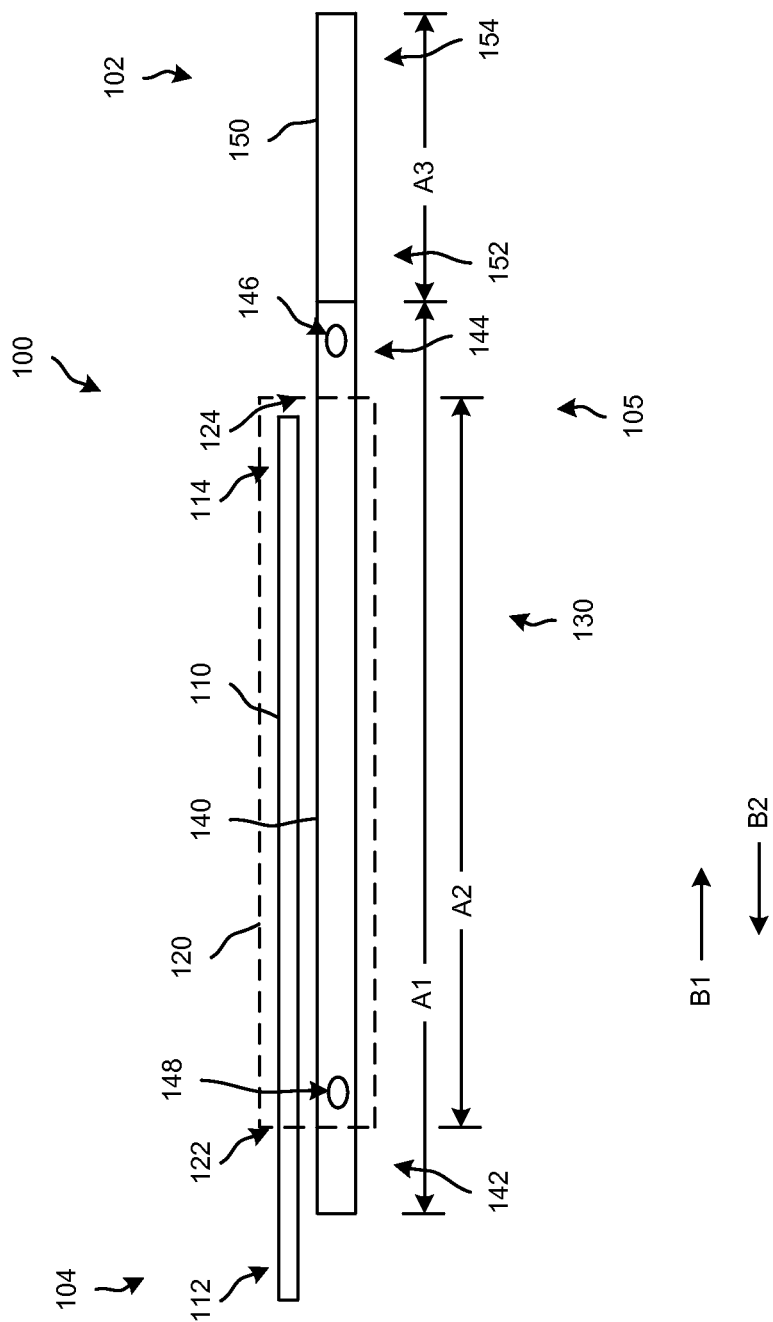
FIG. 1 is a schematic diagram of a medical device in accordance with an implementation.

FIG. 1 is a schematic diagram of a medical device 100 in accordance with an implementation. The medical device 100 includes an implant 110 (or a portion thereof), a sleeve 120, and a delivery member 130. The delivery member 130 includes a tube portion 140 and a dilator portion 150. The dilator portion 150, which has a proximal portion 152 and a distal portion 154, is coupled to the tube portion 140. The tube portion 140 has a distal portion 144 and a proximal portion 142. The distal portion 144 of the tube portion 140 is coupled to the proximal portion 152 of the dilator portion 150. The sleeve 120 has a distal end 124 and a proximal end 122, and the implant 110 has a proximal portion 112 and a distal portion 114. At least a portion of the implant 110 and at least a portion of the delivery member 130 are disposed within a lumen (within a lumen portion) defined by the sleeve 120.

In some implementations, the sleeve 120 and the delivery member 130, which can be coupled together (e.g., removably coupled together, fixedly coupled together), can be collectively referred to as a sleeve assembly 105. In some implementations, the implant 110 can include a mesh (e.g., a polypropylene mesh, a mesh where one or more edges is detanged, a mesh where opposite edges are asymmetrically detanged). The implant 110, the sleeve 120, and the delivery member 130 are aligned parallel to (e.g., substantially parallel to) one another.

In some implementations, the medical device 100 shown in FIG. 1 can be a portion of a medical device. For example, the portion can be a first portion that is mirrored in a second portion of the medical device. In other words, the portion of the medical device (or portions thereof) can be mirrored in another portion of the medical device 100. In some implementations, the medical device 100 can be coupled to other medical devices or can include other portions (e.g., mesh, sleeves, etc.) that are not mirrored or non-symmetrical.

In some implementations, the implant 110 included in the medical device 100 can be used to suspend various bodily tissues or organs in a body of a patient. For example, in some implementations, the implant 110 can be used to suspend a pelvic organ of a patient's body. In some implementations, the implant 110 can be a retropubic incontinence sling. In some implementations, the implant 110 (and at least some portions of the medical device 100) can be configured to be delivered by way of a transvaginal approach, a transobturator approach, vaginal pre-pubic approach, or can be delivered through other approaches and positioned at various locations within a patient's body. In some implementations, the medical device 100 (e.g., the implant 110) can be use for various types of prolapse conditions such as uterine prolapse, cystoceles, rectoceles, and vaginal vault prolapse.

The medical device 100 includes a first end portion 102 and a second end portion 104. The medical device 100 can be moved inside (e.g., interior to) a body of a patient with the first end portion 102 piercing through one or more bodily tissues (e.g., an incision within a bodily tissue). The second end portion 104 can also be moved into the body by piercing through one or more bodily tissues.

In some implementations, the medical device 100 (or a portion thereof) can be configured to be coupled to a delivery device (not shown) for movement (e.g., delivery) of the medical device 100 inside a body of a patient. In various implementations, the delivery device can be configured to deliver the implant 106 to a delivery site or to a location (e.g., position) within the body of the patient so that at least a portion of the implant 110 can be coupled to (e.g., affixed to) a bodily tissue. The medical device 100 can be inserted inside a patient's body from a first incision and at least a portion (e.g., the first end portion 102) of the medical device 100 can be extended out of the patient's body through a second incision. In some implementations, the first incision can be a vaginal incision. In some implementations, the second incision can be an abdominal incision or a groin incision. More details related to a delivery device are described below and in connection with, for example, FIG. 6.

After the medical device 100 (or a portion thereof) has been inserted into a body of a patient, the sleeve 120 and/or the delivery member 130 can be removed while at least a portion of the implant 110 remains in the body of the patient. In some implementations, the sleeve 120 (or a portion thereof) and the delivery member 130 (or a portion thereof) can be concurrently removed. In some implementations, the sleeve 120 (or a portion thereof) can be removed before the delivery member 130 (or a portion thereof) is removed, or vice versa.

The implant 110 can be removably coupled to the sleeve and/or the delivery member 130. In some implementations, the implant 110 can be removably coupled to the sleeve and/or the delivery member 130 via a coupling mechanism (not shown). In some implementations, the implant 110 can be irreversibly coupled to the sleeve 120 and/or the delivery member 130 so that after being decoupled, the implant 110 may not be recoupled to the sleeve and/or the delivery member 130. In some implementations, the implant 110 can be reversibly coupled to the sleeve 120 and/or the delivery member 130 so that after being decoupled, the implant 110 may be recoupled to the sleeve and/or the delivery member 130. More details related to a coupling mechanism are described in connection with, for example, FIG. 2. In some implementations, a coupling mechanism can be referred to as a locking mechanism.

In this implementation, the tube portion 140 of the delivery member 130 can define a lumen. The tube portion 140 of the delivery member 130 can include, or define, a first opening 146 and a second opening 148. In other words, the first opening 146 and the second opening 148 can be defined within a sidewall of the tube portion 140. A fluid (e.g., an anesthetic, a cleansing fluid, an antibiotic, a medication, a glue), can be introduced into the tube portion 140 via the first opening 146 and/or the second opening 148. The fluid can be introduced into the tube portion 140 during a medical procedure. In some implementations, the first opening 146 can be, or can function as, an inlet port or opening through which a fluid is introduced, and the second opening 148 can be, or can function as, an outlet port or opening through which the fluid can be delivered.

As shown in FIG. 1, the first opening 146 is disposed between the distal end 124 of the sleeve 120 and the proximal portion 142 of the dilator portion 150 of the delivery member 130. In this implementation, the first opening 146 is disposed between a distal portion 114 of the implant 110 and the proximal portion 152 of the dilator portion 150. In some implementations, the first opening 146 in the tube portion 140 can be disposed between the proximal end 122 of the sleeve 120 and the distal end 124 of the sleeve 120. Accordingly, the first opening 146 can be disposed within a lumen (within a lumen portion) defined by the sleeve 120. In such implementations, an opening (not shown) can be included in (e.g., defined within) the sleeve 120 that corresponds to the first opening 146 so that a fluid delivery device can be coupled to the first opening 146 via the opening included in the sleeve 120.

The second opening 148 within the tube portion 140 is disposed within the lumen defined by the sleeve 120. In some implementations, the second opening 148 can be disposed outside of the sleeve 120. In such implementations, the second opening 148 can be included in a portion of the tube portion 140 that is proximal to the proximal end 122 of the sleeve 120. In some implementations, more openings than those shown in FIG. 1 can be defined by or included in the tube portion 140. The opening(s) can be disposed inside (e.g., interior to) or outside of (e.g., exterior to) the lumen defined by the sleeve 120. Although not shown, in some implementations, the dilator portion 150 can include one or more openings through which a fluid can be introduced and/or delivered. Although shown as being on the same side of the delivery member 130 of the medical device 100, in some implementations, one or more openings such as first opening 146 and second opening 148, can be on different sides of the delivery member 130 of the medical device.

In some implementations, fluid delivery can be performed during a medical procedure as follows. After the medical device 100 (or a portion thereof) has been inserted into a body of a patient, the sleeve 120 and/or the delivery member 130 can be decoupled from the implant 110. As the sleeve 120 and/or the delivery member 130 are/is being removed (e.g., pulled) from the body of the patient, a fluid, such as a medication or an anesthetic, can be injected into the tube portion 140 via the first opening 146 (which can be accessible to an operator external to the body of the patient). Accordingly, the fluid can be introduced into the body of the patient via the second opening 148 (which can be internal to the body of the patient). In some implementations, the fluid can flow into at least a portion of a lumen defined by the sleeve 120 and then into the body of the patient. In other words, the fluid can flow out of the second opening 148 into at least a portion of a lumen defined by the sleeve 120 and then into the body of the patient. If the second opening 148 is disposed outside of the sleeve 120, the fluid can flow out of the second opening 148 directly into the body of the patient without (or substantially without) being introduced into an interior portion of the sleeve 120.

In some implementations, injection of a fluid can be continuously performed as the sleeve 120 and/or the delivery member 130 are/is being removed (e.g., removed continuously or intermittently) from a body of a patient. In some implementations, injection of a fluid can be performed at intervals (e.g., time intervals, during discrete and separate time periods) as the sleeve 120 and/or the delivery member 130 are/is being removed (e.g., removed continuously or intermittently) from a body of a patient. In some implementations, a volume of fluid that is being delivered can be gauged using a fluid delivery device such as a graduated syringe.

In some implementations, after placing the implant 110 in a body of a patient and after delivering a fluid inside the body of the patient, portions (e.g., first end portion 102) of the medical device 100 that protrude out through an incision can be pulled out of the body of the patient. At least some components of the medical device 100 such as the sleeve 120 and/or the delivery member 130 can be decoupled from the implant 110 after placing the implant 110 so that the components can be removed while the implant 110 remains inside of the body of the patient. In some implementations, placement of the implant 110 can be adjusted (e.g., tensioning and/or positioning can be performed) after delivering a fluid inside a body of a patient and after the sleeve 120 and/or the delivery member 130 have been decoupled from the implant 110 (and removed from the body of the patient). In some implementations, placement of the implant 110 can be adjusted before delivery of a fluid inside a body of a patient and/or before the sleeve 120 and/or the delivery member 130 have been decoupled from the implant 110 (and removed from the body of the patient). In some implementations, the fluid can be injected (into the first opening 146 and out of the second opening 148), onto at least a portion of the implant 110, and into tissue surrounding the implant 110 during the removal of the sleeve 120 and the delivery member 130.

As another specific example, the medical device 100 can be placed in a body of a patient such that a direction of the delivery of the fluid is different from a direction of delivery of the medical device 100 inside the patient's body. The medical device 100 (or a portion thereof) can be inserted inside the patient's body from a vaginal incision (e.g., a first incision) and moved towards an abdominal incision (e.g., a second incision). The medical device 100 may be advanced from the vaginal incision toward the abdominal incision in the first direction (e.g., direction B1). A portion (e.g., a portion of the sleeve 120 and/or a portion of delivery member 130) of the medical device 100 may extend out of the abdominal incision after the medical device 100 reaches (e.g., is proximate to) the abdomen of the patient's body. A fluid delivery device (not shown) can be coupled to the first opening 146 of the tube portion 140 (and/or another portion of the medical device 100) to provide a fluid through the tube portion 140. While the fluid delivery device is coupled to the first opening 146 of the tube portion 140 (which can be proximate the abdominal incision), the fluid injected via the first opening 146 and into the tube portion 140 can move along a second direction (e.g., direction B2) from the abdominal incision to the vaginal incision. The first direction and the second direction can be substantially different from one other. In some implementations, the first direction can be opposite the second direction.

In some implementations, the fluid injected through the first opening 146 and along the tube portion 140 moves from the second incision to the first incision along a curved path (e.g., a substantially curved path, a curved path defined by the tube portion 140) inside the patient's body. The curved path can be defined by the medical device 100 as the medical device 100 is delivered from the first incision to the second incision along the curved path. In such cases, the direction that the fluid traces along the curved path during injection of the fluid is different from the direction of delivery of the medical device 100 along the curved path.

The dilator portion 150 can be included in the medical device 100 so that an operator can maneuver the medical device 100 for placing the implant 110 at a delivery site within a body of the patient. The dilator portion 150 can include a tip (not shown) at the distal portion 154 of the dilator portion 150 that can be used to separate tissue and facilitate insertion of the medical device 100 into a body of the patient through the tissue. In some implementations, a delivery device or a delivery needle can be coupled to the dilator portion 150 and can be used for delivering the medical device 100. In some implementations, the dilator portion 150 of the delivery member 130 can be used to define a path along which the implant 110 can be delivered and along which a fluid can be delivered via the tube portion 140 of the delivery member 130.

The proximal portion 142 of the tube portion 140 is surrounded by the proximal end 122 of the sleeve 120, and the distal portion 144 of the tube portion 140 is surrounded by the proximal end 122 of the sleeve 120. A length A1 of the tube portion 140 is greater than a length A2 of the sleeve 120. Accordingly, at least a portion of the tube portion 140 extends outside of the sleeve 120. In some implementations, the length A1 can be less than or equal to the length A2 of the tube portion 140. In addition, as shown in FIG. 1, a length A3 of the dilator portion 150 is less than the length A1 of the tube portion 140 of the delivery member 130. In some implementations, the length A3 can be greater than or equal to the length A1 of the tube portion 140. In this implementation, the length A1 of the tube portion 140 of the delivery member 130, which is partially housed within the sleeve 120, is sufficiently long to, for example, extend from above an abdominal wall (e.g., beyond skin level) to a vagina of a patient such that one or more fluid can be passed from the first opening 146 (which is disposed outside of the body of the patient) to the second opening 148 (which is disposed inside of the body of the patient).

In some implementations, the tube portion 140 of the dilator portion 150 can be separately formed and then joined together, and can be included the delivery member 130 after being joined together. In some implementations, the tube portion 140 and the dilator portion 150 can be monolithically formed from a single material. In some implementations, the tube portion 140 and/or the dilator portion 150 of the delivery member 130 can be made of, for example, a flexible polymer that can maintain lumen patency. In some implementations, a lumen defined by the tube portion 140 can have a relatively constant diameter (e.g., exterior diameter, interior diameter) or cross-sectional profile along a length of the tube portion 140. In some implementations, the lumen defined by the tube portion 140 can have a diameter or cross-sectional profile that varies along the length of the tube portion 140.

In some implementations, one or more portions of the delivery member 130 (e.g., tube portion 140, dilator portion 150) can have a circular cross-sectional shape or profile. In some implementations, one or more portions of the delivery member 130 can have a non-round cross-sectional shape or profile (e.g., a flat shape or profile, a square shape or profile). In some implementations, one or more portions of the delivery member 130 can be collapsible. For example, the tube portion 140 can be made of a material such that the tube portion 140 can collapse or flex when a force is applied and/or can inflate or change shape when a fluid is injected therein.

The medical device 100 can be configured to be coupled to an injection hub (not shown). Specifically, the first opening 146 can be coupled to an injection hub through which a fluid can be delivered into the tube portion 140 of the delivery member 130. In some implementations, the injection hub can be coupled to, or can be part of, a fluid delivery device. In some implementations, the injection hub can be coupled to, or can be part of, the tube portion 140. In other implementations, the medical device 100 can include a portion (e.g., the sleeve 120) that has a sheet of material, which may be porous or non-porous. More details related to an injection hub are described in connection with, for example FIGS. 4 and 5.

Although the delivery member 130 is shown as having at least a portion disposed within the sleeve 120 as part of the sleeve assembly 105. In some implementations, the delivery member 130 can be entirely disposed outside of the sleeve 120. In such implementations, at least a portion of the delivery member 130 can be aligned along and/or coupled to an outside (e.g., exterior) surface of the sleeve 120. In some implementations, the tube portion 140 and/or the dilator portion 150 can be integrated into or as part of the sleeve 120. For example, the tube portion 140 and/or the dilator portion 150 can be molded into the sleeve 120.

In some embodiment the tube portion 140 can be separate from the dilator portion 150. In other words, the tube portion 140 can be a component included in the sleeve assembly 105 separate from the dilator portion 150. In such implementations, the tube portion 140 and the dilator portion 150 can each (and separately) be coupled to the sleeve 120.

Figure 2:
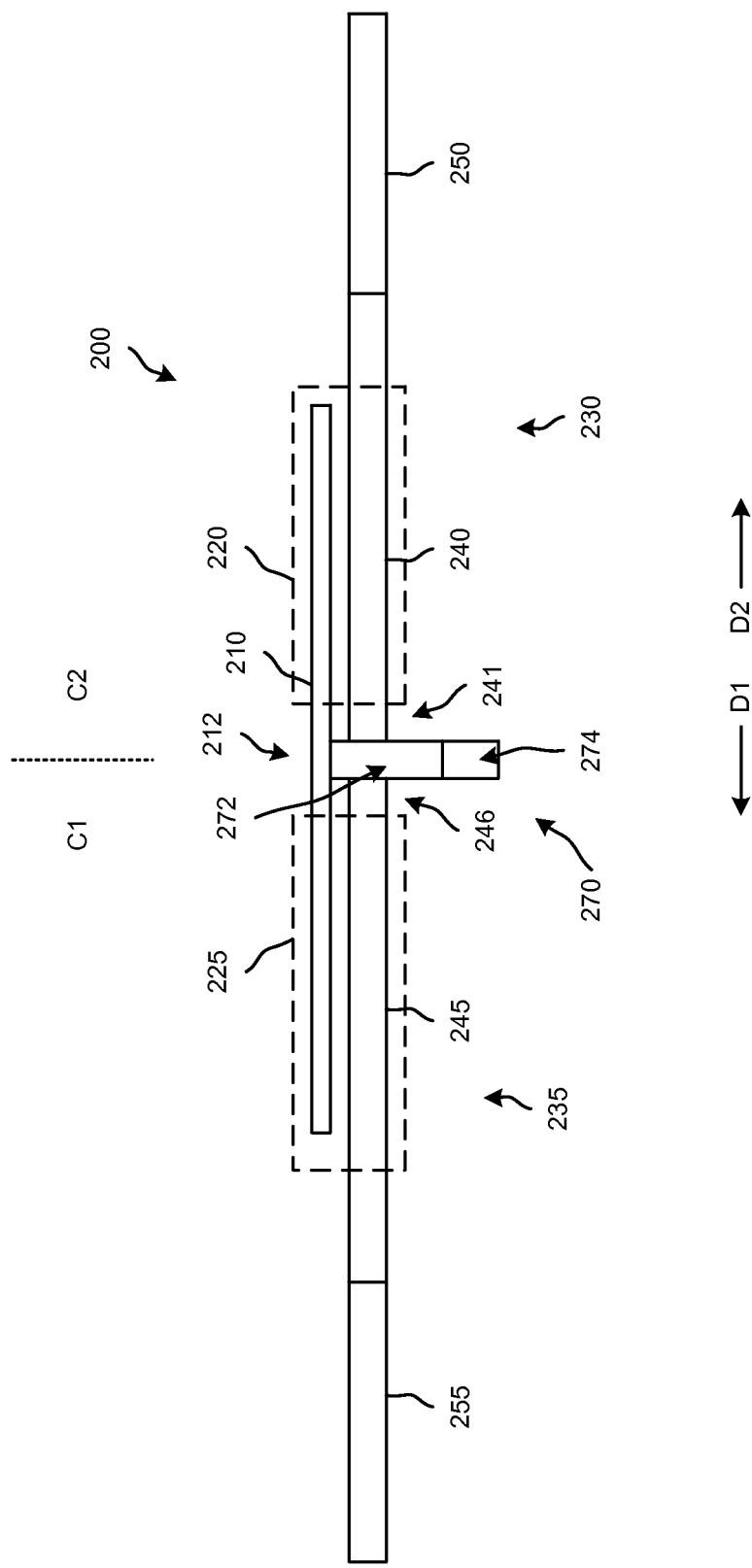
FIG. 2 is a schematic diagram of another medical device in accordance with an implementation.

FIG. 2 is a schematic diagram of another medical device 200 in accordance with an implementation. The medical device 200 can be a variation of the medical device 100 shown in FIG. 1. The medical device 200 has components that are mirrored between a side C1 of the medical device 200 and a side C2 of the medical device 200. In other words, at least some portions of medical device 200 are symmetrical. In some implementations, portions of medical device 200 that are on side C1 can be referred to as side C1 portions of the medical device 200. Similarly, portions of medical device 200 that are on side C2 can be referred to as side C2 portions of medical device 200.

The medical device 200 includes an implant 210, a sleeve 220, a sleeve 225, a delivery member 230, and a delivery member 235. The delivery member 230 includes a tube portion 240 and a dilator portion 250, and the delivery member 235 includes a tube portion 245 and a dilator portion 255. In this implementation, openings within the tube portions 240, 245 are not shown.

As shown in FIG. 2, the medical device 200 includes a coupling mechanism 270. The coupling mechanism 270 includes a base component 272 (which can also be referred to as a tab or as a center tab) and a release mechanism 274. The base component 272 is coupled to a portion of the implant 210. Specifically, the base component 272 is coupled to a medial portion 212 (or middle portion) of the implant 210. Also, the tube portion 240 has a proximal portion 241 coupled to the base component 272, and the tube portion 245 has a proximal portion 246 that is also coupled to the base component 272. The release mechanism 274 (also can be referred to as a decoupling mechanism) of the coupling mechanism 270, when actuated, decouples (or releases) one or more of the tube portion 240, the tube portion 245, or the implant 210 from the base component 272.

In some implementations, the sleeves 220, 225 can be respectively coupled to the delivery members 230, 235 so that the sleeves 220, 225 are coupled to the base component 272 via the delivery members 230, 235. In some implementations, one or more of the sleeves 220, 225 can be coupled to the base component 272. As shown in FIG. 2, the tube portion 240 of the delivery member 230 is disposed between the coupling mechanism 270 and the dilator portion 250 of the delivery member 230. Specifically, the tube portion 240 of the delivery member 230 is coupled to the coupling mechanism 270 and the dilator portion 250 of the delivery member 230

In some implementations, the release mechanism 274 of the coupling mechanism 270 can be actuated during a medical procedure. For example, side C1 portions of the medical device 200 (e.g., the delivery member 235, the sleeve 225, and a portion of the implant 210 on side C1) can be at least partially disposed within a body of the patient along direction D1. After the side C1 portions of the medical device 200 have been moved into the body of the patient, the release mechanism 274 can be used to decouple the delivery member 235 from the base component 272 so that the delivery member 235 can further be moved outside of the body of the patient along direction D1 while a fluid is injected into the body of the patient along direction D2 via the tube portion 245 of the delivery member 235. The delivery member 235 can be moved outside of the body of the patient through a first incision (e.g., a skin incision). In some implementations, the sleeve 225 can be coupled to the delivery member 235 so that as the delivery member 235 is moved outside of the body of the patient, the sleeve 225 is also moved outside of the body of the patient. In addition, the coupling mechanism 270 or a portion thereof (e.g., the base component 272, the release mechanism 274) can be decoupled from the medical device 300 and removed vi a second incision (e.g., a vaginal incision). Accordingly, the medical device 300 can be inserted into a body of a patient and some components (e.g., portions of the delivery member 330) can be moved out of the body of the patient via a first incision and other components (e.g., portions of the coupling mechanism 370) can be moved out of the body of the patient via a second incision.

In some implementations, the release mechanism 274 can be actuated after the side C1 portions of medical device 200 and the side C2 portions of the medical device 200 have been moved into a body of a patient on contra lateral sides of the body of the patient. Injection of a fluid can also be performed on the contra lateral sides as the delivery member 230 and the delivery member 235 are being moved outside of the body of the patient.

In some implementations, the release mechanism 274 can include, for example, a latch, a suture, a suture loop, a spring-loaded mechanism, a gear, and/or so forth. In some implementations, the medical device 200 can include more than one release mechanism. In some implementations, the base component 272 can be coupled to one or more of the sleeve 220, the sleeve 225, the tube portion 240, the tube portion 245 by, for example, a latch, a suture, a suture loop, a spring-loaded mechanism, a gear, a press fit, and/or so forth.

As shown in FIG. 2, the delivery member 230 can extend up to the base component 272. In some implementations, the delivery member 230 can have a length such that the delivery member 230 does not extend up to the base component 272. In such implementations, a space can be disposed between, for example, a proximal end of the delivery member 230 and an outer wall of the base component 272.

Figure 3A:
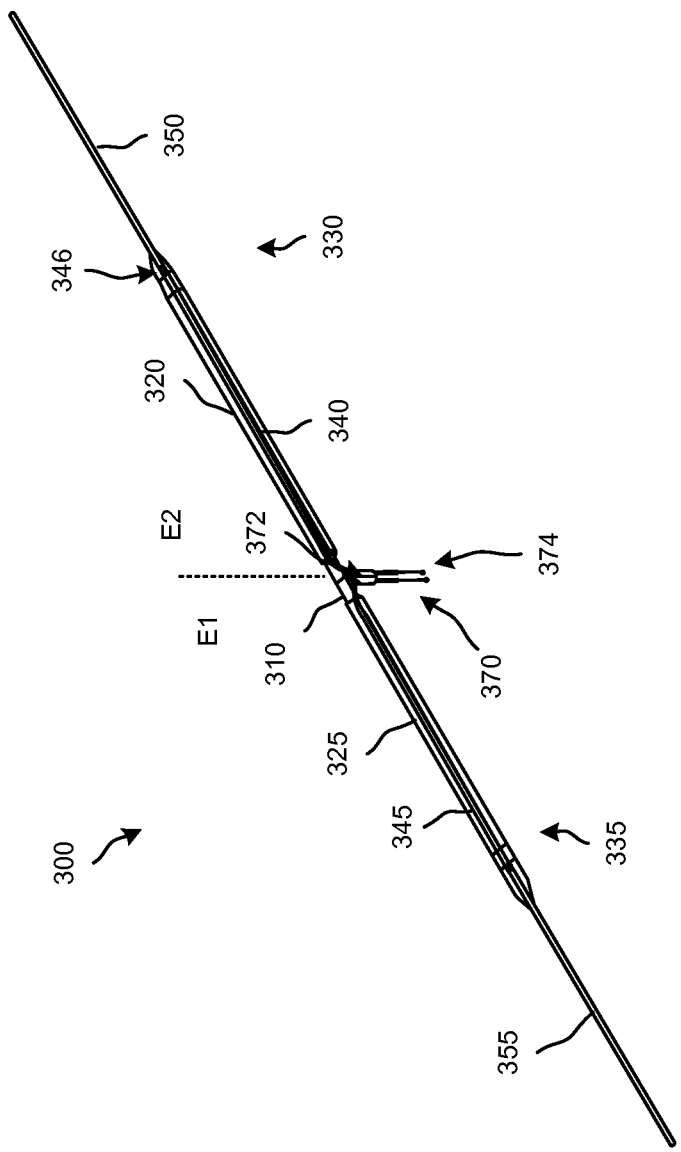

FIGS. 3A through 3D are various views of a medical device 300 in accordance with an implementation. As shown in FIG. 3A, which is a perspective view of the medical device 300, the medical device 300 has components that are mirrored between a side E1 of the medical device 300 and a side E2 of the medical device 300. As shown in FIG. 3A, the medical device 300 includes a coupling mechanism 370. The coupling mechanism 370 includes a base component 372 and a release mechanism 374. The medical device 300 includes sleeves 320, 325, and delivery members 330, 335.

FIG. 3B is a diagram that illustrates a zoomed in view of the side E2 portions of the medical device 300. As shown in FIG. 3B, a portion 347 of the tube portion 340 is configured to be disposed in a lumen 373 (also can be referred to as a channel) of the base component 372. Although not labeled in FIG. 3B, the base component 372 includes multiple lumen (e.g., lumen 373) into which delivery members (e.g., delivery member 330) can be disposed. In some implementations, the base component 372 can be, or can include, a center tab that can be used, for example, for adjustment of the implant 310 after the implant 310 has been placed in a body of the patient. As the delivery member 330 is decoupled from the medical device 300 and removed during a medical procedure, the portion 347 of the tube portion 340 can be moved (e.g., slidably moved) out of the lumen 373 of the base component along direction F1. In some implementations, the portion 347 of the tube portion 340 can be coupled to the base component 372 via a component in addition to, or instead of, the lumen 373 such as a latch, a suture, an adhesive, and/or so forth.

In this implementation, a suture 375 (e.g., a thread) has a portion 378 at least partially disposed within a lumen of the tube portion 340. The suture 375 also has a portion 377 disposed outside of the tube portion 340 (via two openings in the tube portion 340 (which are discussed in more detail in connection with FIG. 3D)) and configured to couple (e.g., fixedly couple) the tube portion 340 and the sleeve 320 to the implant 310. The suture 375, when pulled along direction F2 (which is opposite direction F1), can be pulled out of (e.g., removed from, slidably moved out of) the tube portion 340 so that the tube portion 340 and the sleeve 320 are released from the implant 310. The suture 375 can have an end component 379 (e.g., a ball, a knot) that can be used by an operator to pull the suture 375 out of the tube portion 340. The suture 375 can be a portion of a release mechanism. In some implementations, the suture 375 can be referred to as a rip cord.

The suture 375 can be a type of connecting member. In some implementations, any type of connecting member, such as a wire, a thread, etc. can be used in addition to, or instead of, the suture 375.

Although a suture (e.g., suture 375) is illustrated as being used to release each of the sleeve assemblies in the implementation (for a total of two sutures) shown in connection with FIGS. 3B, in some implementations, a single suture can be incorporated into a medical device to release multiple sleeve assemblies. In some implementations, more than two sutures can be used to release different components associated with a sleeve assembly of medical device.

For example, when it is time to release the sleeve 320 from the implant 310 during a medical procedure, an operator can grasp the suture 375 at any point along the suture 375 and/or the end component 379 and pull along direction F2 to entirely (or partially) remove the suture 375. This disengages the suture 375 from the sleeve 320 and the implant 310, permitting the sleeve 320 and the delivery member 330 to be moved relative to the implant 310. The operator may elect to inject a fluid onto the implant 310 and surrounding tissue as the sleeve 320 and/or delivery member 330 are removed from the implant 310.

In this implementation, a suture 376 (e.g., a thread, a leader), which can be a portion of another release mechanism, can be threaded through the implant 310 so that the implant 310 is coupled to the base component 372. When the suture 376 is cut, the implant 310 (e.g., a medial portion 312 of the implant 310) can be released from the base component 372.

Figure 3C:
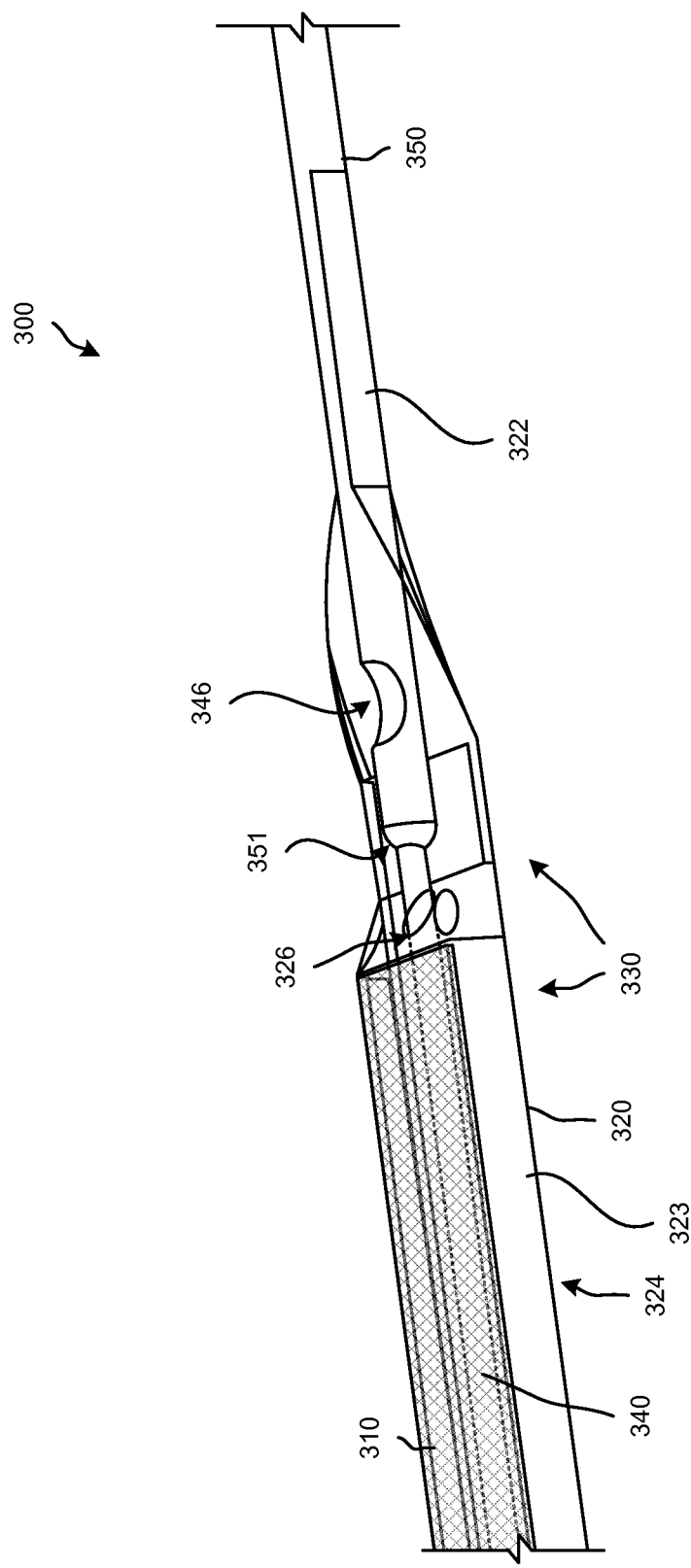

FIG. 3C is a diagram that illustrates a zoomed in view of the medical device 300 around an opening 346 in the delivery member 330. The opening 346 can be an inlet port through which a fluid can be introduced into the tube portion 340 of the delivery member 330. In some implementations, fluid delivery can be performed during a medical procedure as follows. After the medical device 300 (or a portion thereof) has been inserted into a body of a patient, the sleeve 320 and/or the delivery member 330 can be decoupled from the implant 310. As the sleeve 320 and/or the delivery member 330 are/is being removed (e.g., pulled) from the body of the patient, a fluid, such as a medication or an anesthetic, can be injected into the tube portion 340 via the opening 346 (which can be accessible to an operator external to the body of the patient). In some implementations, the fluid can flow into at least a portion of a lumen defined by the sleeve 320 and then into the body of the patient.

As shown in FIG. 3C, the sleeve 320 has an extension portion 322 coupled to a portion of the delivery member 330 and a lumen portion 323 disposed around the tube portion 340. In this implementation, the extension portion 322 of the sleeve 320 is coupled to the dilator portion 350 of the delivery member 330. The extension portion 322, in this implementation, is wrapped around or folded around at least a portion of a circumference of the dilator portion 350. At least a portion of the dilator portion 350 is exposed where the extension portion 322 of the sleeve 320 is not bonded. In some implementations, the extension portion 322 of the sleeve 320 can be coupled to the dilator portion 350 of the delivery member 330 using an adhesive, heat bonding, a press fit, a friction fit, and/or so forth. In some implementations, the extension portion 322 of the sleeve 320 can be coupled to the tube portion 340 of the delivery member 330 in addition to being coupled to the dilator portion 350 of the delivery member 330. In some implementations, the extension portion 322 of the sleeve 320 can be coupled to the tube portion 340 of the delivery member 330 instead of being coupled to the dilator portion 350 of the delivery member 330.

The opening 346 is disposed between the extension portion 322 of the sleeve 320 and the dilator portion 350 of the delivery member 330 that is coupled to (or wrapped around) the delivery member 330. In some implementations, because the sleeve 320 and the delivery member 330 can be coupled together the sleeve 320 and the delivery member 330 can be collectively referred to as a sleeve assembly.

In this implementation, the opening 346 is included in the dilator portion 350 of the delivery member 330, and the dilator portion 350 defines at least a portion of a lumen that is in fluid communication with the tube portion 340 of the delivery member 330. The opening 346 is disposed between the extension portion 322 of the sleeve and a portion 324 of the sleeve 320 within which the delivery member 330 and the implant 310 are disposed.

In this implementation, the tube portion 340 of the delivery member 330 extends through (or is disposed within) an opening 326 of the sleeve 320. In some implementations, the opening 326 of the sleeve 320 can be larger than shown in FIG. 3C. In some implementations, the sleeve 320 can have or include multiple linings or layers through which an opening (e.g., opening 326) can be disposed so that the delivery member 330 can extend their through.

The dilator portion 350 has a diameter greater than a diameter of the tube portion 340. The dilator portion 350 can be coupled at location 351 to the tube portion 340. The dilator portion 350 can be coupled to the tube portion 340 using, for example, a heat bonding process or can be extruded in a single piece with a taper. In some implementations, the dilator portion 350 can have as a diameter less than or equal to a diameter of the tube portion 340.

Figure 3D:
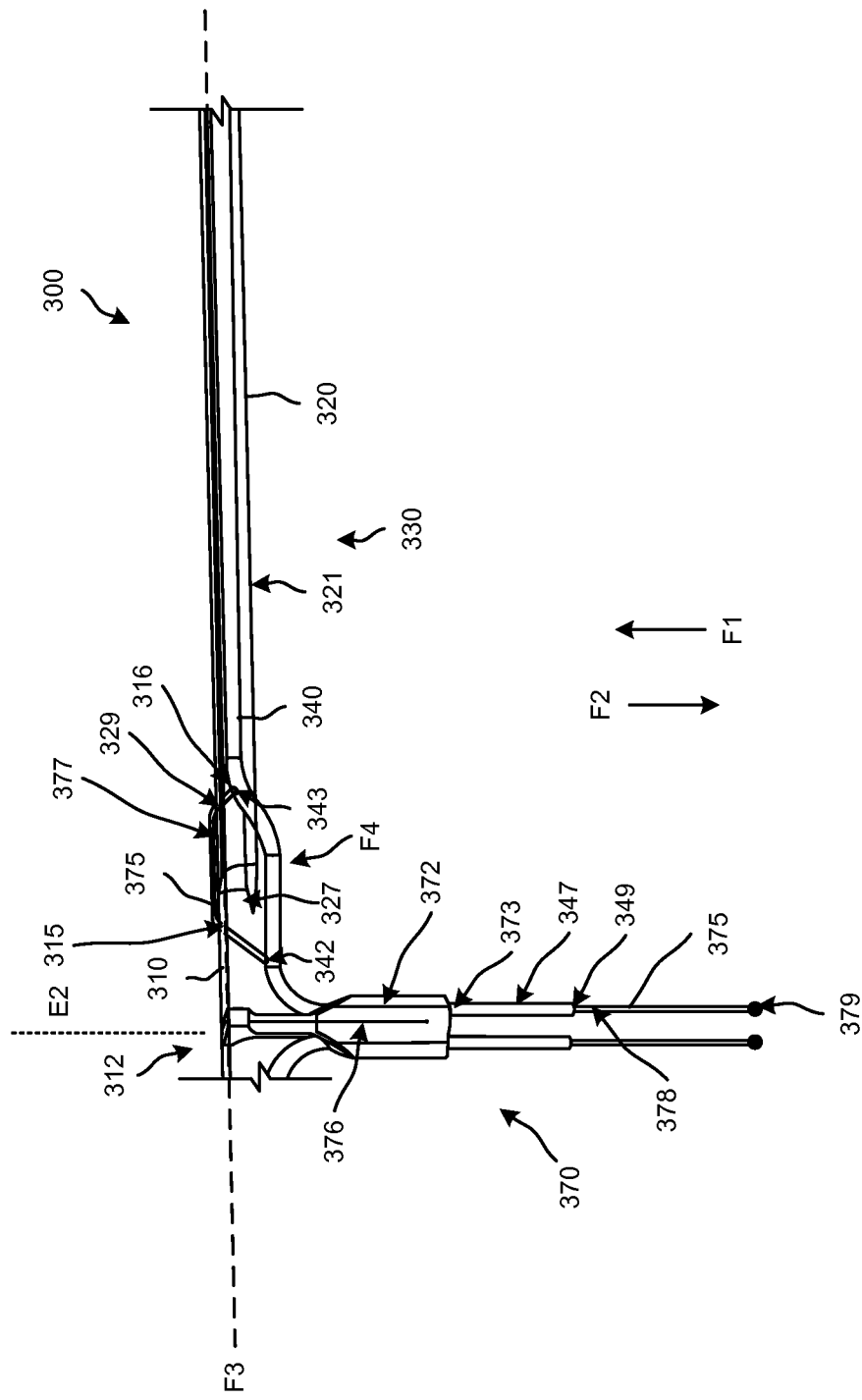

FIG. 3D is a diagram that illustrates a zoomed in view of the side E2 portions of the medical device 300. As shown in FIG. 3D, the portion 347 of the tube portion 340 is disposed in the lumen 373 of the base component 372.

In this implementation, the suture 375 has the portion 378 at least partially disposed within a lumen of the tube portion 340. When the suture 375 is pulled along direction F2, the suture 375 can be pulled through two openings—an opening 342 and an opening 343. In some implementations, a fluid delivered into the tube portion 340 can move through one or more of the openings 342, 343 and/or an opening at a proximal end 349 of the tube portion 340. As shown in FIG. 3D, the opening 343 is disposed within a lumen of the sleeve 320 and the opening 342 is disposed outside of the lumen of the sleeve 320.

As shown in FIG. 3D, the portion 377 of the suture 375 is disposed on at least a portion of the sleeve 320 and is disposed on at least a portion of the implant 310. Also, the portion 377 of the suture 375 is disposed above the implant 310 so that the implant 310 is disposed between the portion 377 of the suture 375 and the tube portion 340. Said differently, the implant 310 is aligned along a plane F3 that is disposed between the portion 377 of the suture 375 and the tube portion 340. In this implementation, the suture 375 is inserted through at least one or more openings (e.g., openings 315, 316) in the implant 310 and/or one or more openings (e.g., opening 329) in the sleeve 320 so that the portion 377 of the suture 375 can be exposed outside of the sleeve 320 and the implant 310. Accordingly, the suture 375 is threaded through the proximal end 349 of the tube portion 340, out of the opening 342, through the implant 310 (at opening 315), through the opening 329 of the sleeve 320, through the implant 310 (at opening 316), and into the opening 343 of the tube portion 340.

In some implementations, the tube portion 340 can be sealed off or closed at approximately point F4 using a blocking component (e.g., a plug) (not shown) so that a fluid that is injected into the tube portion 340 of the delivery member 330 exits (or moves through) opening 343, but cannot exit opening 342 or an opening at the proximal end 349 of the tube portion 340. In other words, the blocking component can block or divide a portion of a lumen in the tube portion 340 so that one portion of the tube portion 340 is no longer in fluid communication with another portion of the tube portion 340. In some implementations, more than one blocking component can be included in the tube portion 340. Accordingly, a fluid injected into the tube portion 340 can exit the opening 343 and an opening 327 of the sleeve 320. As noted above, additional openings (e.g., holes, ports) can be located along one or more portions of the tube portion 340 and/or along the sleeve 320 through which one or more fluids injected into the tube portion 340 can exit.

As shown in FIG. 3D, at least a portion of the tube portion 340 is disposed in (or is inserted through) an opening within a bottom portion 321 of the sleeve 320. Accordingly, a first portion of the tube portion 340 is disposed within a lumen defined by the sleeve 320 and a second portion of the tube portion 340 is disposed outside of the lumen defined by the sleeve 320. Said differently, the bottom portion 321 of the sleeve 320 is disposed between the first portion of the tube portion 340 and the second portion of the tube portion 340. As shown in FIG. 3D the tube portion 340 has multiple curved portions along a path between the base component and the dilator portion 350 (not shown).

As shown in FIG. 3D the implant 310 and the tube portion 340 are aligned along the plane F3. Also, the implant 310 is disposed above the base component 372 so that the base component 372 is disposed between the proximal end 349 of the tube portion 340 and the implant 310.

Because the implant 310 (or the medial portion 312 thereof) is exposed (e.g., not covered by one or more sleeves), the implant 310 can be configured to contact a urethra of the patient while permitting the delivery member 330 to be coupled to the coupling mechanism 370. Also, because the medial portion 312 of the implant 310 is exposed and is not covered by one or more sleeves (e.g., sleeve 320), the medial portion 312 of the implant 310 can be stretched, and/or tensioned. Also, the movement (e.g., tensioning) of the medial portion 312 of the implant 310 when being implanted into a body of the patient can be visually and physically gauged. In some implementations, a level of stretching or tensioning of the exposed portion of the implant 310 (e.g., the medial portion 312 of the implant 310) can be controlled by, for example, detanging one or more edges of the implant 310. The medial portion 312 of the implant 310 can be detangled to control a level of stretching of the medial portion 312 (e.g., detanged portions of the implant 310 can have more stretch). Also, because the portion 347 of the tube portion 340 can slidably move within the lumen 373 of the base component 372, an operator can, for example, stretch the medial portion 312 of the implant 310 to a desired tension while visually and physically gauging the tension of the implant 310 (underneath a urethra the body of the patient). In some implementations, a portion of an implant (e.g., implant 310) that is exposed between sleeves (e.g., sleeve 320) of a medical device (e.g., medical device 300) can have a length that is greater than a length of one or more of the sleeves.

In this implementation, the portion 347 the tube portion 340 is aligned along a longitudinal axis that is orthogonal to or substantially orthogonal to other portions of the tube portion 340 (which are aligned along the plane F3). As illustrated in FIG. 3D, the tube portion 340 has a length such that the tube portion 340 extends up to and is coupled to the coupling mechanism 370. The length of the tube portion 340 is defined so that the tube portion 340 would extend beyond the coupling mechanism 370 if not disposed within the lumen 373 of the base component 372.

To decrease tension on the implant 310 during a medical procedure, before release of the sleeve 320 and/or the delivery member 330 using the suture 375, an operator can grasp a portion the portion 347 of the tube portion 340 and/or the base component 372 and move (e.g., pull, push) in direction F1 or direction F2. By moving in direction F1 or direction F2, the implant 310, sleeve 320, and/or delivery member 330 can be moved toward or away from a portion of a body of a patient such as a vagina or urethra. In some implementations, the entire medical device 300 can be removed from (e.g., moved out of) a body of patient without damaging, the sleeve 320 covered implant 310, by moving the medical device 300 (via the portion 347 of the tube portion 340 and/or the base component 372) in direction F2.

In some medical procedures, after the sleeve 320 and/or the delivery member 330 have been removed (e.g., released), the base component 372 can remain attached to the medial portion 312 of the implant 310. An operator may grasp the base component 372 to adjust (e.g., loosen) the implant 310, if by any chance, the implant 310 was further tensioned during removal of the sleeve 320 and/or the delivery member 330. The base component 372 can be removed by cutting the suture 376 (which can be a leader (on one or more both sides)) and removing the base component 372. In other implementations the base component 372 may not have (e.g., may exclude) the lumen 373 therethrough. In some implementations, the base component 372 may be excluded from the medical device 300. Implementations excluding a base component are described in more detail below.

Figure 4:
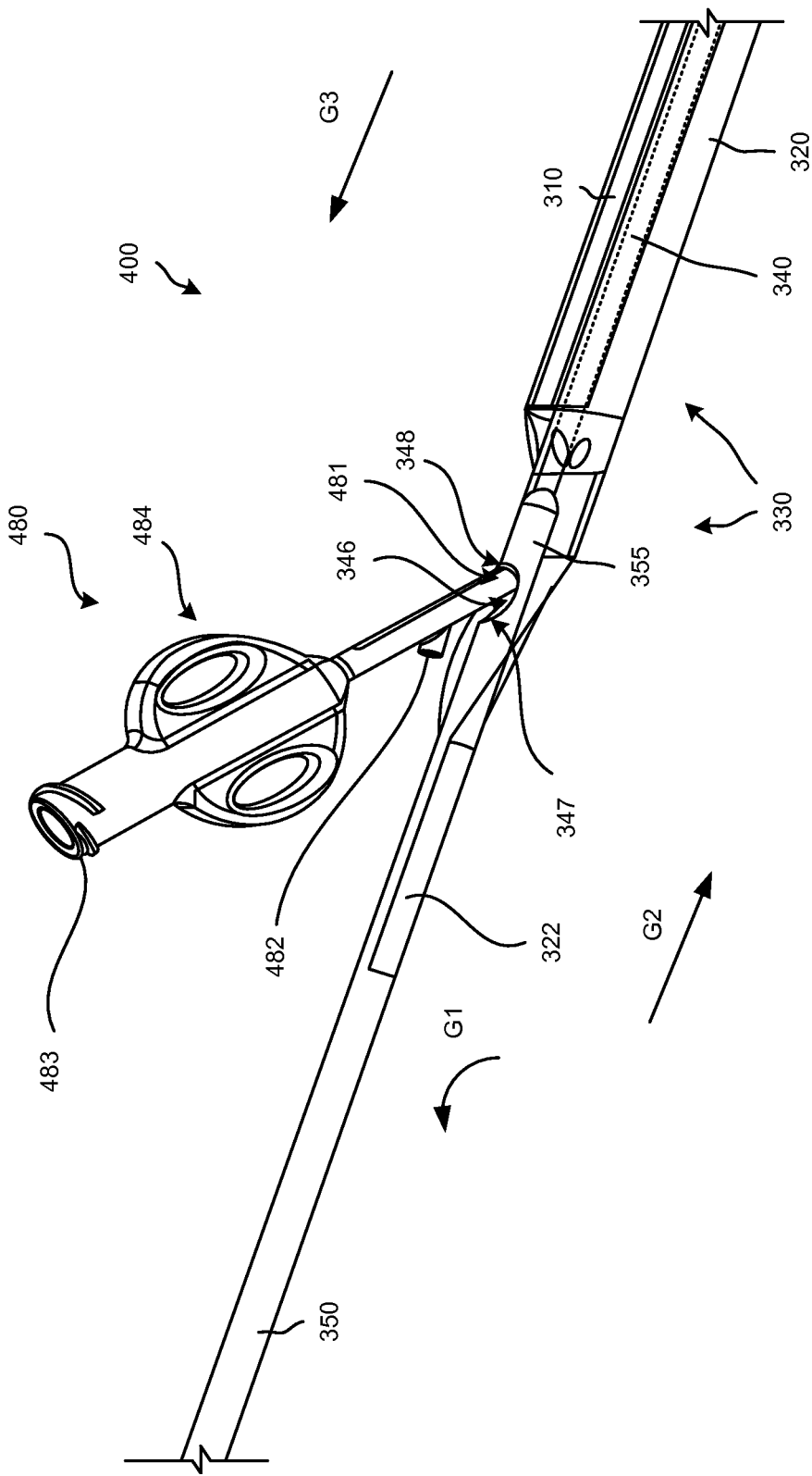
FIG. 4 is a diagram illustrating an injection hub coupled to a portion of the medical device shown in FIGS. 3A through 3D.

FIG. 4 is a diagram illustrating an injection hub 480 coupled to a portion of the medical device 300 shown in FIGS. 3A through 3D according to an implementation. The injection hub 480 can be used to facilitate injection of a fluid into the medical device 300 using a fluid delivery device. The injection hub 480 can also be used to facilitate removal of the sleeve 320 and/or the delivery member 330. The medical device 300 includes an implant 310, a sleeve 320, a delivery member 330 (which includes a tube portion 340 and a dilator portion 350). The sleeve 320 has an extension portion 322 coupled to the dilator portion 350 of the delivery member 330.

As shown in FIG. 4, a tip portion 481 of the injection hub 480 can be inserted into (e.g., coupled to) an opening 346 in the dilator portion 350. In some implementations, the opening 346 can be referred to as a port. A fluid delivery device (e.g., a syringe) including a fluid (not shown) can be attached to a coupler 483 of the injection hub 480. The fluid delivery device can be used to deliver the fluid via the injection hub 480 into the medical device 300. In some implementations, the coupler 483 of the injection hub 480 can be, or can include, a male coupler, a female coupler, a thread-able engagement, a snap fit mechanism, a frictional fit mechanism, and/or so forth. The injection hub 480 includes a handle 484 that can be used by an operator to grasp and maneuver the injection hub 480 during a medical procedure.

In some implementations, the dilator portion 350 can be moved (e.g., bent) in the direction of arrow G1 and returned in the opposite direction of arrow G1 to allow port edge 347 to be coupled to (e.g., encompass) a protrusion 482 of the injection hub 480 to maintain the injection hub 480 coupled to the delivery member 330. The protrusion 482 of the injection hub 480 can be coupled to the port edge 347 while an operator is injecting and pulling the sleeve 320 and/or the delivery member 330 from the implant 310 and out of a body of a patient in direction G3 (using at least in part the injection hub 480). The direction G3 is opposite the direction of injection along direction G2. The injection procedure can be repeated similarly on a contra lateral side (not shown).

Figure 5:
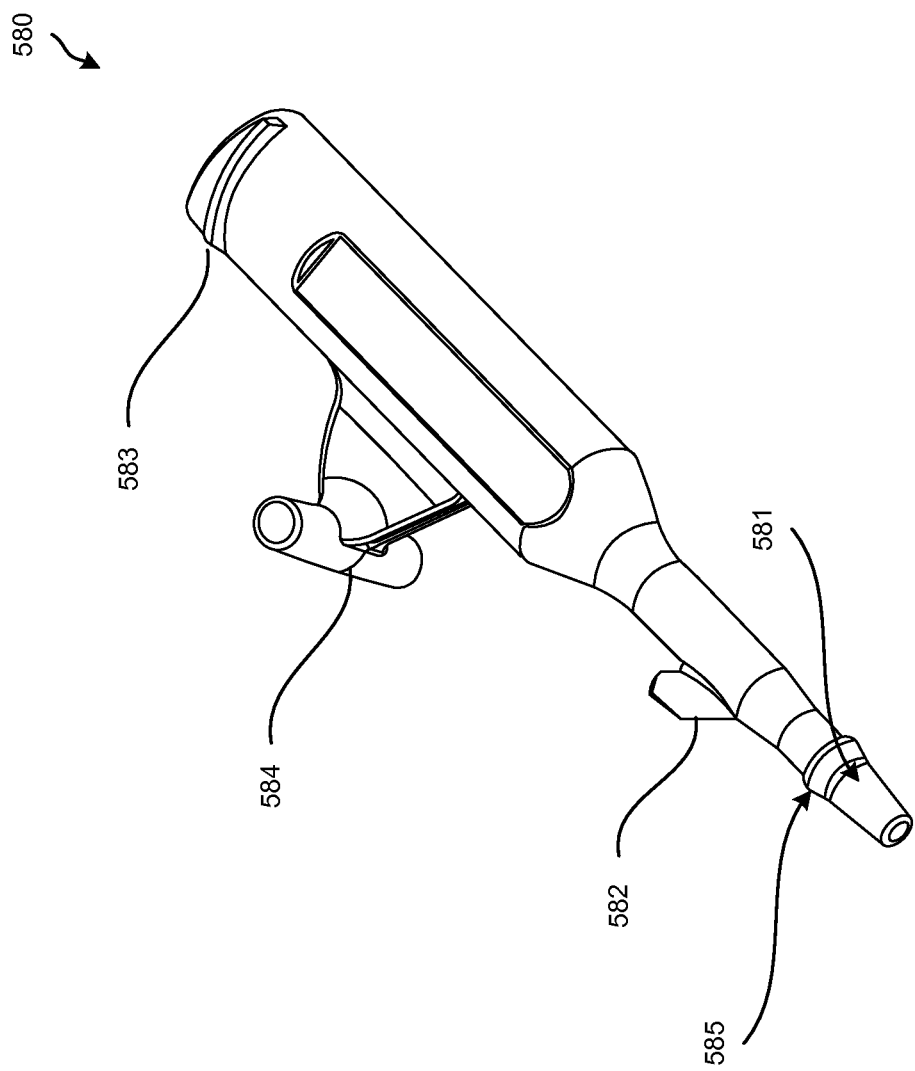
FIG. 5 is a diagram illustrating another injection hub.

FIG. 5 is a diagram illustrating another injection hub 580 according to an implementation. The injection hub 580 can be used to facilitate injection of a fluid into a medical device using a fluid delivery device.

As shown in FIG. 5, a tip portion 581 of the injection hub 580 can be inserted into (e.g., coupled to) an opening of a dilator portion of a delivery member. The injection hub 580 includes a protrusion 585 that can facilitate coupling of the injection hub 580 (or the tip portion 581) to the opening of the dilator portion of the delivery member. A fluid delivery device (e.g., a syringe) including a fluid (not shown) can be attached to a coupler 583 of the injection hub 580. The injection hub 580 includes a handle 584 that can be used by an operator to grasp and maneuver the injection hub 580 during a medical procedure.

As shown in FIG. 5, the injection hub 580 includes a protrusion 582. In some implementations, a dilator portion of a delivery member (not shown) can be moved (e.g., bent) so that an opening is coupled to the protrusion 582 of the injection hub 580 to maintain the injection hub 580 in desired position with respect to the delivery member during a medical procedure. Specifically, the protrusion 582 of the injection hub 580 can be coupled to the delivery member while an operator is injecting and pulling a sleeve and/or the delivery member out of a body of a patient during the medical procedure.

Figure 6:
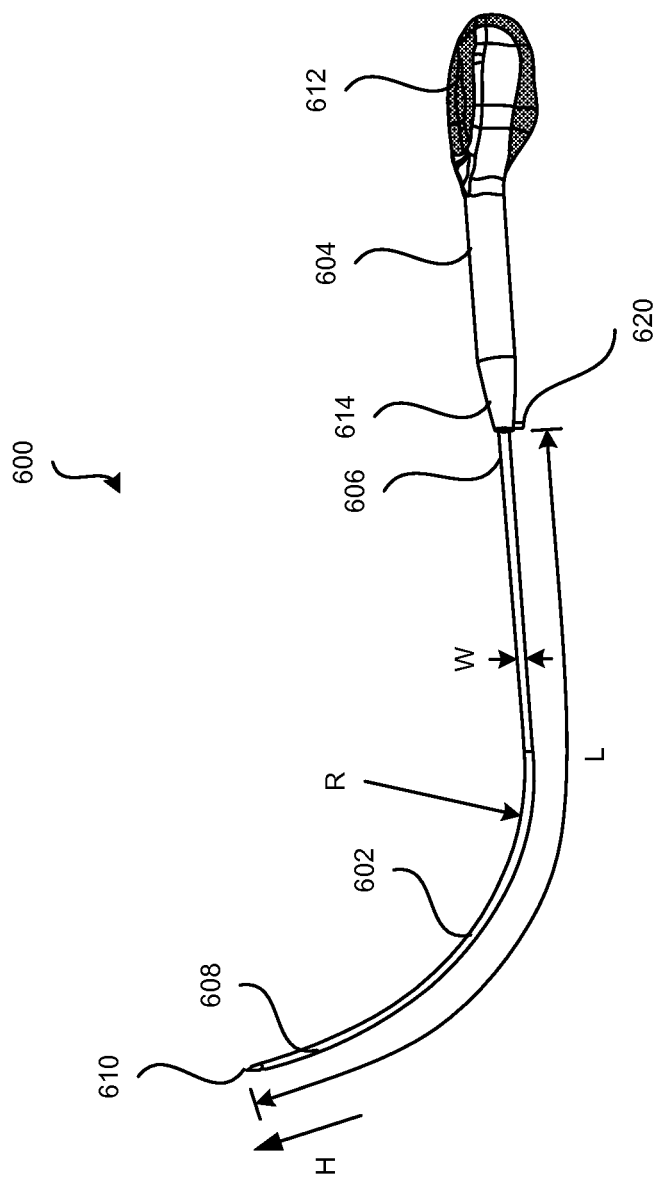
FIG. 6 is a perspective view of a delivery device.

FIG. 6 is a perspective view of a delivery needle or a delivery device 600. The delivery device 600 can be configured to deliver a medical device (e.g., medical device 100, medical device, etc.) to a target location inside a body of a patient. The delivery device 600 includes a needle 602 and a handle 604. In some implementations, the needle 602 can be configured to be inserted into a dilator portion of a delivery member (e.g., the dilator portion 350 of the delivery member 330 of FIGS. 3A through 3D) for guiding the dilator portion and the implant toward a target site inside a body of a patient. In some implementations, the needle 602 can be inserted into a lumen of the dilator portion from a proximal portion of the dilator portion and advanced into the lumen until the needle 602 reaches the distal portion of the dilator portion. In some implementations, as mentioned above, the needle 602 can pierce through a closed end tip of a dilator portion. In some implementations, the needle 602 can be received into a needle slot of a dilator portion. In some implementations, the needle 602 can be configured to be coupled to a sleeve of a medical device.

The needle 602 has a proximal portion 606 and a distal portion 608. The needle 602 may include a tip portion 610 at the distal portion 608. In some implementations, the tip portion 610 may be sharp and configured to dissect tissue layers and create a passageway within bodily tissues to deliver and place an implant (e.g., implant 310) inside a body of a patient.

In some implementations, the needle 602 can be made of stainless steel or other medical grade material. The needle 602 can define a length L and a width W. In some implementations, the needle 602 defines a curved profile and defines a radius of curvature R. The width W, the length L, and the curvature R of the needle 602 can depend on one or more surgical requirements. In some implementations, the width W and length L of the needle 602 can vary based on an internal diameter of a lumen of a dilator portion of a delivery member.

In some implementations, the needle 602 can be configured to be used in a transvaginal retro pubic approach. In some implementations, the needle 602 can be configured so as to be adapted to be used in the transobturator approach or vaginal pre-pubic approach. In some implementations, the needle 602 can be configured to be used in delivering an implant through various other approaches inside a body of a patient. In some implementations, the delivery device 600 can be a surgical needle 602 with a relatively small outer diameter for minimally invasive surgery.

In some implementations, the needle 602 can be configured to frictionally engage within a lumen of a dilator portion of a delivery member. In some implementations, the dilator can be configured to be coupled to the needle 602 such that the needle 602 is received inside the lumen of the dilator portion and fixed therein, at least temporarily. In an implementation, the dilator portion can be positioned over (or coupled to) the needle 602 by sliding at least a portion of the dilator portion over the needle 602, thereby forming a removable connection or coupling between the two. In some implementations, a length of a dilator portion can be longer than the length L of the needle 602 such that the dilator portion slides over the needle 602 or other mechanism such as a suture, suture loop, hook, anchor, and/or so forth.

In some implementations, the handle 604 can be made of a plastic material. Exemplary plastic materials include polycarbonate, lexan, acrylonitrile butadiene styrene (ABS), and the like. The handle 604 has a proximal portion 612 and a distal portion 614 such that the distal portion 614 of the handle can be coupled to the proximal portion 606 of the needle 602. The proximal portion 612 of the handle 604 can be configured to remain outside a dilator portion of a delivery member once coupled to the dilator portion so as to remain available for manipulation by an operator.

As shown in FIG. 6, the delivery device 600 includes a protrusion 620. The protrusion 620 can be used to engage an opening in a dilator portion of a delivery member (e.g., opening 346 included in the dilator portion 350 of the delivery member 330 shown in FIG. 3B) during insertion into a body of the patient. Accordingly, the delivery device 600 can be removably coupled to at least a portion of a delivery member of a medical device during a medical procedure. Coupling the delivery device 600 to the delivery member of medical device using the protrusion 620 can prevent (e.g., substantially prevent) inadvertent decoupling of the delivery device 600 from the delivery member during a medical procedure. In some implementations, the protrusion 620 can include a hook, a recess, a curved portion, a flexible portion, a latch, a suture loop, and/or so forth.

As mentioned above, the medical devices described herein (e.g., medical device 100) can be used in a medical procedure including a transobturator approach and/or in a medical procedure for repairing a prolapse condition. In such implementations, an association loop used to move one or more of the medical device can be adapted to an L shape slot delivery device (not shown). In some implementations, one or more of the medical devices can be adapted or modified for a medical procedure including a supra pubic approach. In such implementations, a delivery device used to move one or more of the medical device can include an L shaped slot.

Use of at least a portion of the delivery device 600 with respect to the elements shown in FIG. 4 is described below. In some implementations, the tip portion 610 of the needle 602 can be inserted into, for example, the opening 446 along direction G3 shown in FIG. 4. An end portion 455 of the dilator portion 450 can be bent in the opposite direction of arrow G1 and returned in the direction of arrow G1 to allow port edge 448 to encompass the protrusion 620 of the handle 604. This can couple (e.g., secure) the dilator portion 450 to the handle 604 and prevent (e.g., substantially prevent) an operator from inadvertently pushing the dilator portion 450 off the needle 604 in direction H during insertion. The opening 446 and/or the dilator portion 450 can be removed from the protrusion 620 by bending the end portion 455 of the dilator portion 450 in a direction opposite arrow G1 and sliding the needle 604 out of the opening 446 in the direction of arrow G2.

Figure 7A:
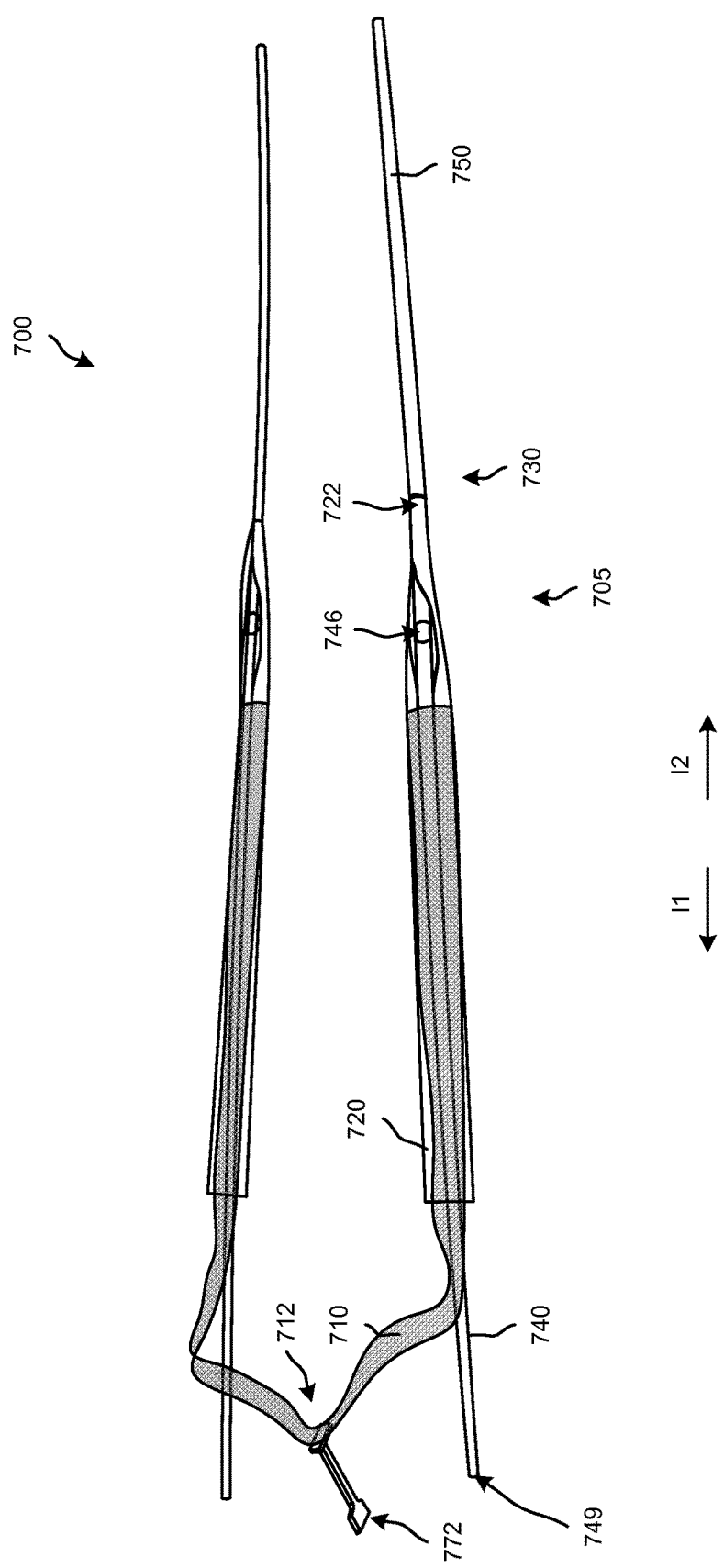
FIGS. 7A through 7C illustrate various views of a medical device, according to an implementation.
Figure 7B:
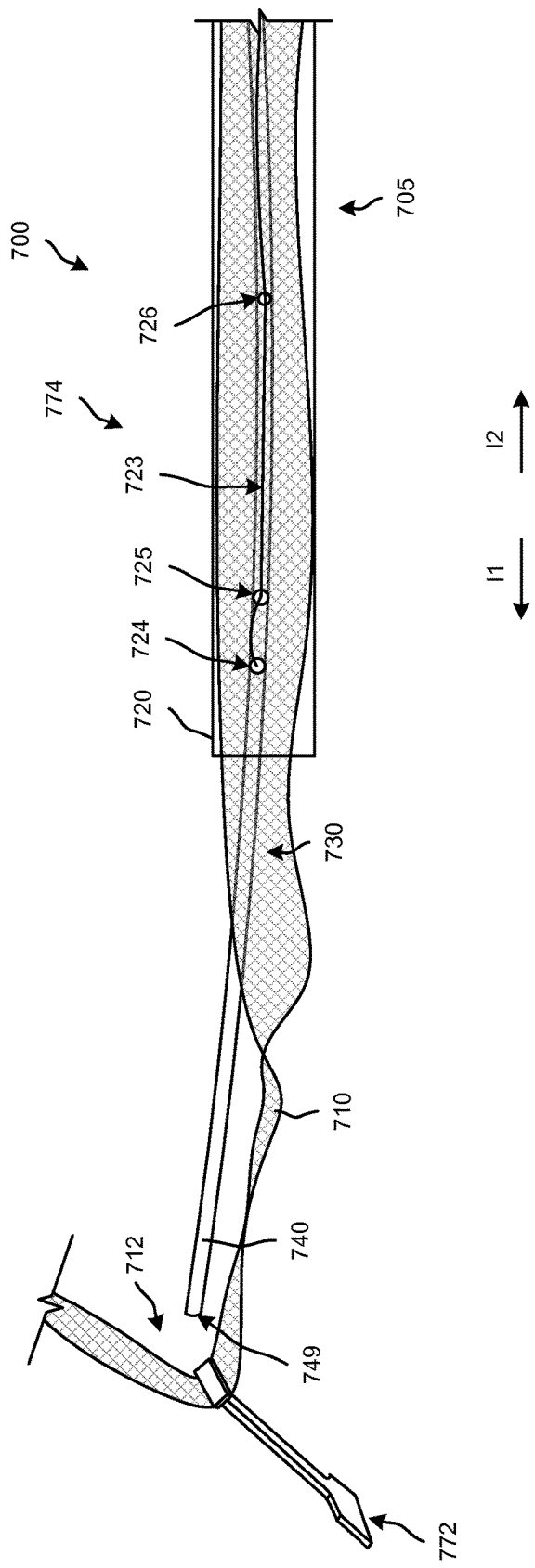
Figure 7C:
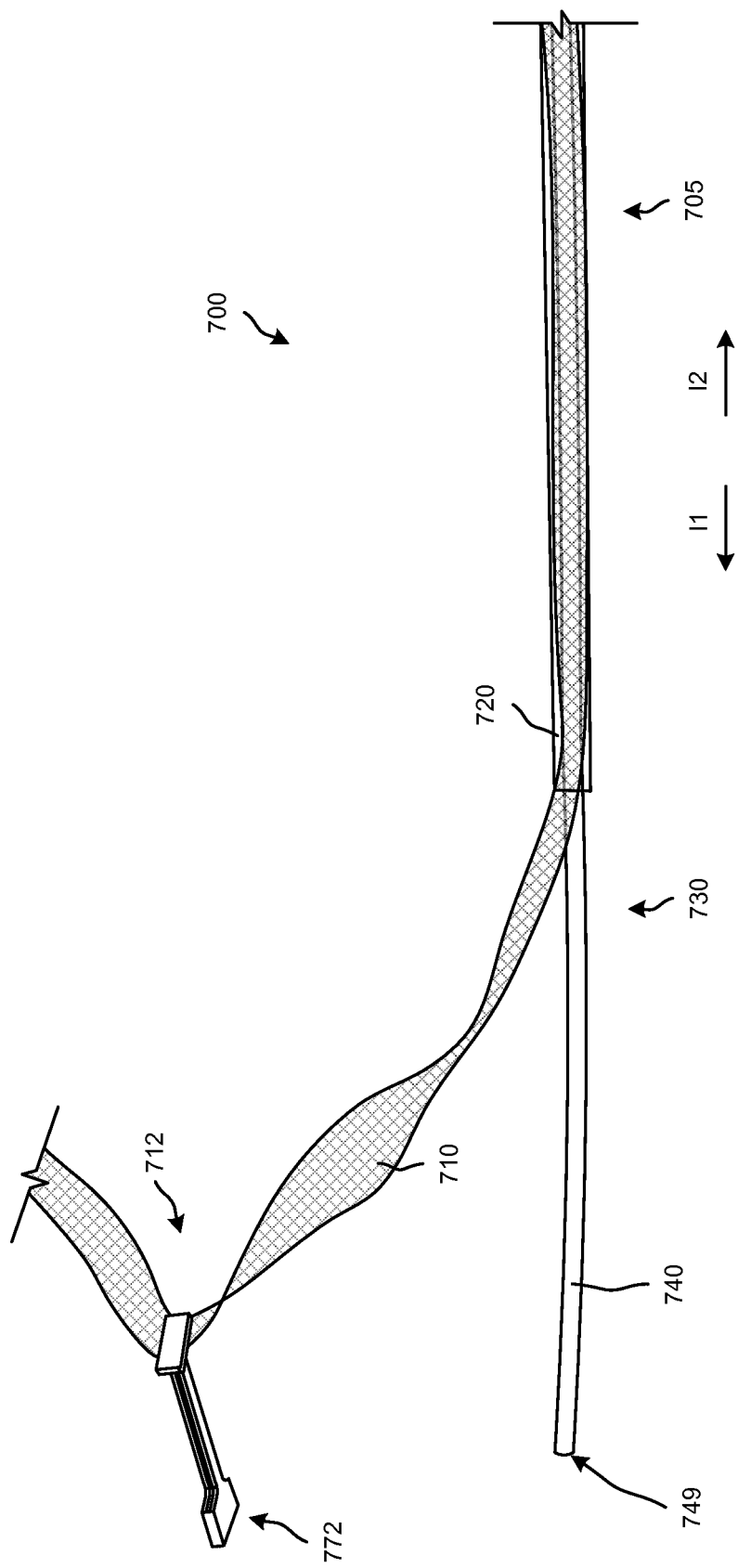

FIGS. 7A through 7C illustrate various views of a medical device 700, according to an implementation. To simplify the description, discussion related to FIG. 7A through 7C will be related to a single side of the medical device 700. However, the features on one side of the medical device 700 are mirrored on the opposite side of the medical device 700.

As shown in FIG. 7A, the medical device 700 includes a sleeve assembly 705. The sleeve assembly 705 includes a sleeve 720 and a delivery member 730. The delivery member 730 includes a tube portion 740 and a dilator portion 750. At least a portion of the sleeve assembly 705 (e.g., at least a portion of the sleeve 720) is disposed around at least a portion of an implant 710.

A fluid can be delivered into the tube portion 740 of the delivery member 730 via an opening 746 included in the tube portion 740. In this implementation, the fluid, after being introduced into the tube portion 740, can exit via an opening at a proximal end 749 of the tube portion 740. Accordingly, the fluid can be delivered into the tube portion 740 along direction I1 while the sleeve assembly 705 is removed from the implant 710 along direction I2 (which is opposite direction I1 or substantially opposite direction I1). Although not shown in FIG. 7A, in some implementations, one or more openings through which a fluid can be delivered can be included in the tube portion 740, instead of, or in addition to, the opening at the proximal end 749. In some implementations, as the fluid is being delivered along direction I1 while the sleeve assembly 705 is being removed from the implant 710 along direction I2, at least a portion of the fluid can exit the opening at the proximal and 749 move into a lumen of the sleeve 720.

A base component 772 is coupled to a medial portion 712 of the implant 710. The base component 772 can be removably coupled to the medial portion 712 of the implant 710. In this implementation, the delivery member 730 is not coupled to the base component 772. In other words, the delivery member 730 as separate from the base component 772. In some implementations, other types of base components can be used in conjunction with the medical device 700 (or any of the other medical devices described herein). For example, in some implementations, the base component 772 can be a suture loop, a protrusion, a hook, and/or so forth.

Although not shown, in some implementations, a medical device (e.g., medical device 700) can exclude a base component (e.g., base component 772). In such implementations, one or more markings on an implant and/or on the delivery member can be used to indicate a medial portion or centerline of an implant (e.g., implant 710).

As shown in FIG. 7A, an extension portion 722 of the sleeve 720 is coupled to at least a portion of the delivery member 730. In some implementations, the extension portion 722 can be coupled to the tube portion 740 and/or the dilator portion 750. In this implementation, the extension portion 722 of the sleeve 720 surrounds the delivery member 730. In some implementations, the extension portion 722 can be coupled to only a portion of an outer profile (e.g., circumference) of the delivery member 730. The opening 746 is exposed through the extension portion 722 so that a fluid delivery device and/or an injection hub can be coupled to the opening 746.

FIG. 7B is a diagram that illustrates a zoomed in view of a portion of the medical device 700. In this implementation, the implant 710 is coupled to the sleeve assembly 705 via a release mechanism 774. As shown in FIG. 7B, at least a portion of the release mechanism 774 is associated with surface of the sleeve 720.

In this implementation, the release mechanism 774 includes a suture 723 (which can be connecting member) that is threaded through openings 724, 725, and 726 in the sleeve 720. In some implementations, the suture 723 can be coupled to (e.g., weaved into) at least a portion of the implant 710. In some implementations, the suture 723 can be coupled to (e.g., wrapped around) at least a portion of the delivery member 730. Accordingly, the sleeve assembly 705 (which includes the sleeve 720 and the delivery member 730) can be released from or decoupled from the implant 710 by severing the suture 723.

In some implementations, the implant 710 can be coupled to the sleeve assembly 705 using a different release mechanism 774 that can include, for example, a latch, a press fit, friction fit, a suture loop, a hook, an adhesive, and/or so forth. In some implementations, more or less openings in those shown in FIG. 7B can be included in the release mechanism 774. In some implementations, the release mechanism 774 can use, or can include, one or more openings in the delivery member 730.

FIG. 7C is a diagram that illustrates a side view of the sleeve assembly 705. As shown in FIG. 7C, the sleeve assembly 705 has a thickness greater than a thickness of the delivery member 730 disposed therein.

Figure 8:
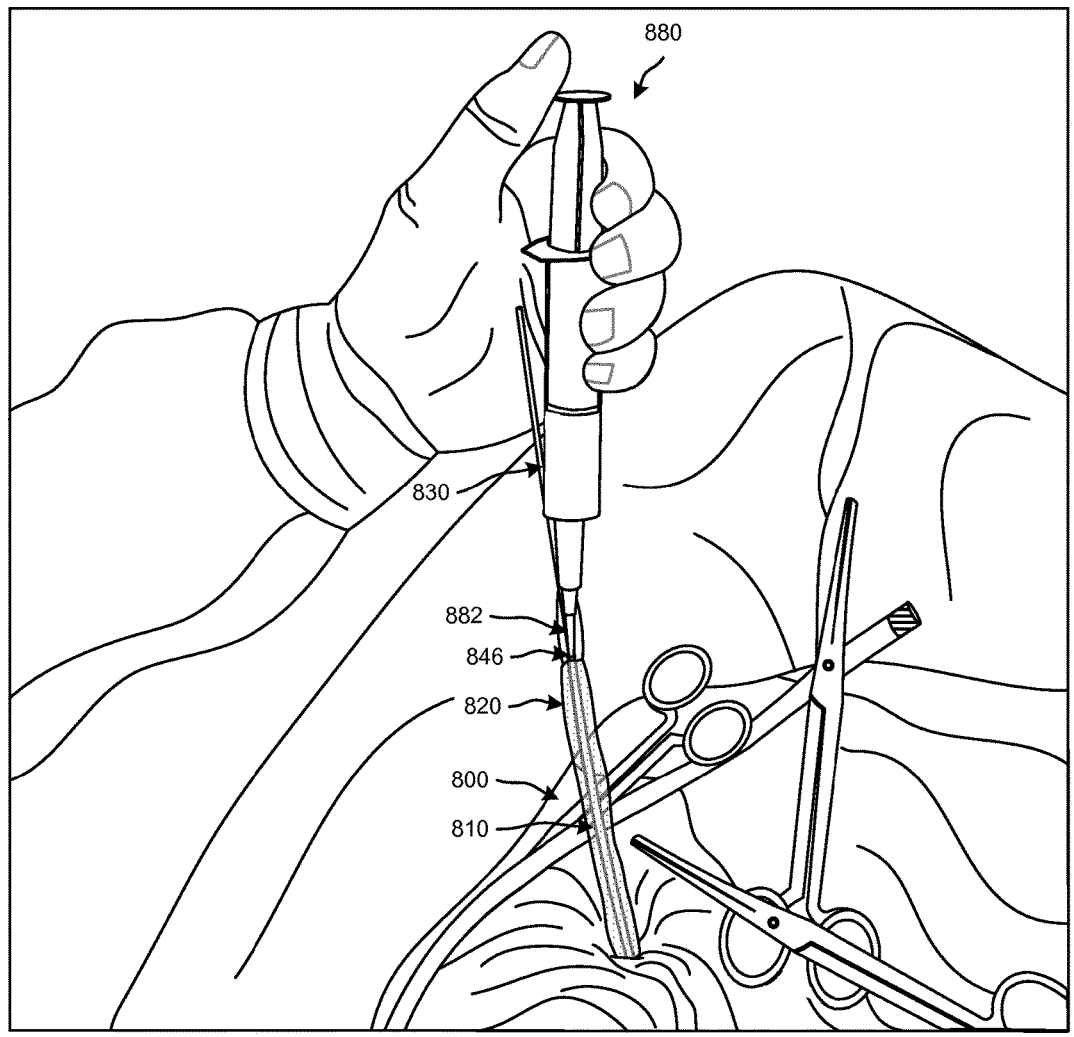
FIG. 8 is a diagram that illustrates a fluid delivery device delivering a fluid into a medical device.

FIG. 8 is a diagram that illustrates a fluid delivery device 880 delivering a fluid into a medical device 800. As shown in FIG. 8, the fluid delivery device 880 has a tip portion 882 coupled to an opening 846 of a delivery member 830 of the medical device 800. As shown in FIG. 8, a sleeve 820 of the medical device 800 is disposed around the delivery member 830 and an implant 810.

Figure 9:
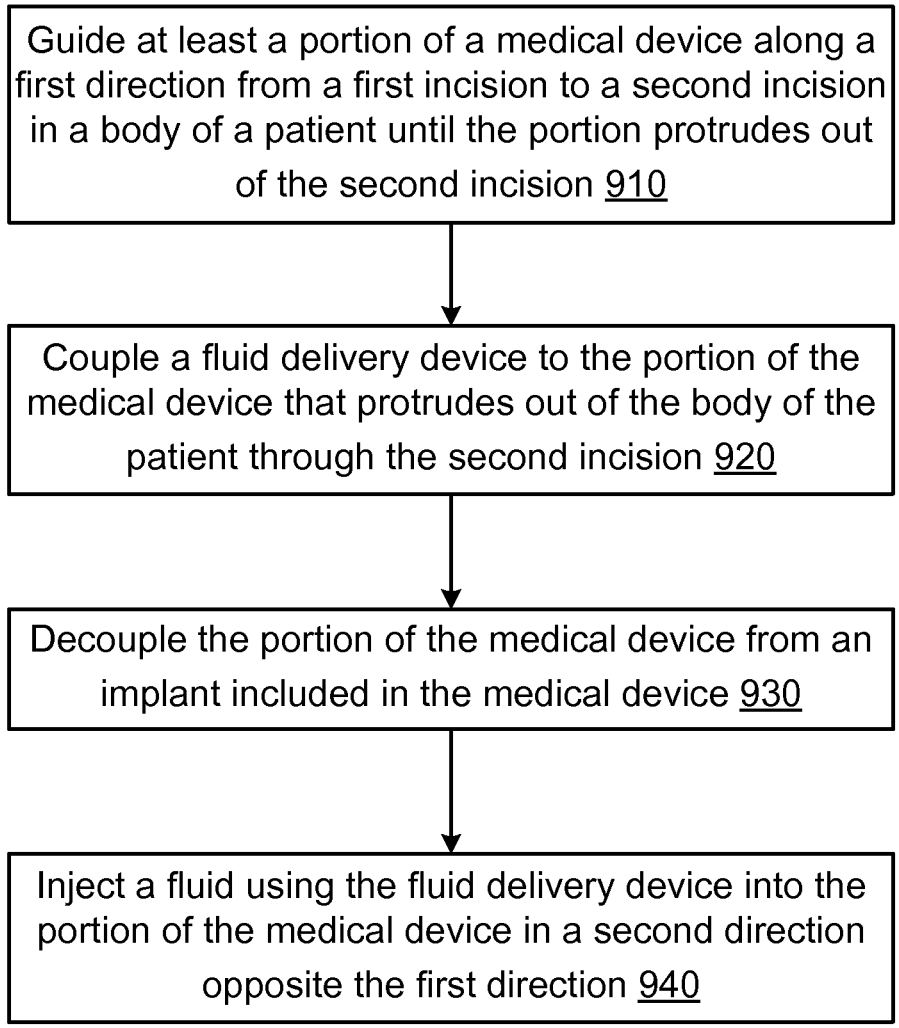
FIG. 9 is a flowchart illustrating a method of treatment of a pelvic floor disorder.

FIG. 9 is a flowchart illustrating a method of treatment of a pelvic floor disorder. As shown in FIG. 9, at least a portion of a medical device can be guided along a first direction from a first incision toward a second incision in a body of a patient until the portion protrudes out of the second incision (block 910). The portion of the medical device can include sleeve assembly, which can include a delivery member and a sleeve. At least a portion of the delivery member and at least a portion of the sleeve can be included in the sleeve assembly. Also, at least a portion of an implant can be disposed within a lumen defined by the sleeve.

In some implementations, the medical device can be guided along a path defined by at least a portion of the delivery member. Specifically, at least a portion of the past can be defined by a dilator portion of the delivery member.

A fluid delivery device can be coupled to the portion of the medical device that protrudes out of the body of the patient through the second incision (block 920). In some implementations, the fluid delivery device can be coupled to an opening included in a tube portion of a delivery member of medical device. In some implementations, the fluid delivery device can be coupled to the opening via an injection hub. The injection hub can be removably coupled to the opening and can be removably coupled to the fluid delivery device.

The portion of the medical device can be decoupled from an implant included in the medical device (block 930). In some implementations, the decoupling can include cutting one or more sutures used to couple the portion of medical device to the implant. In some implementations, the portion of medical device can be decoupled by moving (e.g., slidably moving, pulling, cutting, removing) a release mechanism (e.g., a suture) proximate a medial portion of the implant.

A fluid can be injected using the fluid delivery device into the portion of the medical device in a second direction opposite (or substantially opposite) the first direction (block 940). In some implementations, the first direction can be non-parallel or a different direction to the second direction. In some implementations, the first direction can be orthogonal (or substantially orthogonal) to the second direction. In some implementations, the fluid can be injected in the second direction, using the fluid delivery device, as the portion of the medical device is removed from the body of the patient along the first direction. In some implementations, the portion of medical device can include a tube portion and the fluid can be injected via an opening (e.g., an outlet port) of the tube portion into at least a portion of a lumen of a sleeve.

In one general aspect, a medical device can include an implant having a medial portion and a distal portion. The medical device can include a delivery member including a dilator having a distal portion, and a tube coupled to the dilator. The tube can define a lumen in fluid communication with an opening in the tube. The opening can be disposed between the distal portion of the implant and the distal portion of the dilator of the delivery member. The medical device can include a sleeve having a lumen. The distal portion of the implant and at least a portion of the delivery member can be disposed within the lumen portion of the sleeve.

In some implementations, the lumen of the sleeve is coupled to the tube of the delivery member. In some implementations, the sleeve has an extension portion coupled to the dilator of the delivery member. In some implementations, the sleeve has an extension portion coupled to the lumen of the sleeve. The opening is disposed between the lumen of the sleeve and the distal portion of the dilator of the delivery member.

In some implementations, the dilator and the tube are monolithically formed. In some implementations, the opening is a first opening. The medical device can include a second opening defined within a sidewall of the tube of the delivery member such that the first opening is in fluid communication with the second opening via the lumen of the tube.

In some implementations, the opening is a first opening. The medical device can include a second opening defined within a sidewall of the tube of the delivery member and disposed within the lumen of the sleeve. In some implementations, the opening is configured to receive a fluid delivery device. In some implementations, the tube of the delivery member has a length greater than a length of the lumen of the sleeve.

In one general aspect, a medical device can include an implant. The medical device can include a delivery member including a dilator, and a tube having a proximal portion, a distal portion coupled to the dilator, and a medial portion disposed between the distal portion and the proximal portion. At least the medial portion of the tube defines a lumen. The medical device includes a sleeve having a lumen. The lumen of the sleeve has a distal end and a proximal end. The implant has at least a portion disposed within the lumen, and the medial portion of the tube can be disposed within the lumen of the sleeve. The distal portion of the tube can be distal to the distal end of the lumen of the sleeve, and the proximal portion of the tube can be proximal to the proximal end of the lumen of the sleeve.

In some implementations, the medical device can include a base component coupled to the implant and coupled to the proximal portion of the tube. In some implementations, the medical device can include a base component coupled to the implant and coupled to the proximal portion of the tube. The medical device can include a connecting member coupled to the sleeve and coupled to the proximal portion of the tube.

In some implementations, the medical device can include a first opening in the distal portion of the tube. The first opening can be disposed distal to the distal end of the lumen of the sleeve. The medical device can include a second opening in the medial portion of the tube, and a third opening in the proximal portion of the tube. The third opening can be disposed proximal to the proximal end of the lumen of the sleeve.

In some implementations, the medical device can include a first opening in the medial portion of the tube, a second opening in the proximal portion of the tube, and a connecting member removably coupled to the sleeve. The connecting member can have a first portion disposed in the first opening and a second portion disposed in the second opening.

In some implementations, the opening is a first opening. The medical device can include a second opening defined within a sidewall of the tube and disposed within the lumen of the sleeve. In some implementations, the medical device can include a base component defining a lumen therethrough and configured to receive the proximal portion of the tube.

In some implementations, the medical device can include a connecting member coupled to the sleeve and to the delivery member, and a release mechanism configured to decouple the connecting member from the delivery member when activated.

In another general aspect, a method can include moving a medical device including a sleeve disposed around at least a portion of an implant and a tube of a delivery member along a first direction from a first incision toward a second incision in a body of a patient such that at least a portion of the delivery member protrudes out of the body of the patient through the second incision. The method can include coupling a fluid delivery device to the portion of the delivery member protruding out of the body through the second incision, and injecting a fluid, using the fluid delivery device, into delivery member in a second different from the first direction.

In some implementations, the sleeve is coupled to the delivery member via a connecting member. The method can include decoupling the connecting member from the fluid delivery device. In some implementations, the method can include pulling the implant assembly from the second incision in the first direction while injecting the fluid into the fluid delivery device.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
   an implant having a medial portion and a distal portion;
   a delivery member including:
     a dilator having a distal portion, and
     a tube having a proximal end portion and a distal end portion, the distal end portion of the tube being coupled to the dilator, the tube defining a lumen in fluid communication with an opening in the tube, the opening being disposed between the distal portion of the implant and the distal portion of the dilator of the delivery member;
   a sleeve having a lumen, the distal portion of the implant and at least a portion of the delivery member being disposed within the lumen of the sleeve; and
   a connecting member having a first portion disposed within the lumen of the tube, a second portion disposed outside the lumen of the tube, and a third portion disposed within the lumen of the tube, the second portion being disposed between the first portion and the third portion, the second portion of the connecting member being configured to releasably couple the sleeve and the tube to the implant.

2. The medical device of claim 1, wherein the lumen of the sleeve is coupled to the tube of the delivery member.

3. The medical device of claim 1, wherein the sleeve has an extension portion coupled to the dilator of the delivery member.

4. The medical device of claim 1, wherein the sleeve has an extension portion coupled to the lumen of the sleeve, the opening is disposed between the lumen of the sleeve and the distal portion of the dilator of the delivery member.

5. The medical device of claim 1, wherein the dilator and the tube are monolithically formed.

6. The medical device of claim 1, wherein the opening is a first opening, the medical device further comprising:
   a second opening defined within a sidewall of the tube of the delivery member such that the first opening is in fluid communication with the second opening via the lumen of the tube.

7. The medical device of claim 1, wherein the opening is a first opening,
   the medical device further comprising:
   a second opening defined within a sidewall of the tube of the delivery member and disposed within the lumen of the sleeve.

8. The medical device of claim 1, wherein the opening is configured to receive a fluid delivery device.

9. The medical device of claim 1, wherein the tube of the delivery member has a length greater than a length of the lumen of the sleeve.

10. A medical device, comprising:
an implant;
a delivery member including:
  a dilator, and
  a tube having a proximal portion, a distal portion coupled to the dilator, and a medial portion disposed between the distal portion and the proximal portion, at least the medial portion of the tube defining a lumen;
a sleeve having a lumen of a length, the lumen of the sleeve having a distal end and a proximal end, the implant having at least a portion disposed within the lumen of the sleeve, the tube extending the length of the lumen such that the medial portion of the tube is disposed within the lumen of the sleeve, the distal portion of the tube extending distal to the distal end of the lumen of the sleeve, the proximal portion of the tube extending proximal to the proximal end of the lumen of the sleeve; and
a base component defining a lumen therethrough and configured to receive the proximal portion of the tube.

11. The medical device of claim 10, further comprising:
a connecting member coupled to the sleeve and coupled to the proximal portion of the tube.

12. The medical device of claim 10, further comprising:
a first opening in the distal portion of the tube, the first opening being disposed distal to the distal end of the lumen of the sleeve;
a second opening in the medial portion of the tube; and
a third opening in the proximal portion of the tube, the third opening being disposed proximal to the proximal end of the lumen of the sleeve.

13. The medical device of claim 10, further comprising:
a first opening in the medial portion of the tube;
a second opening in the proximal portion of the tube; and
a connecting member removably coupled to the sleeve, the connecting member having a first portion disposed in the first opening and a second portion disposed in the second opening.

14. The medical device of claim 10, further comprising:
a first opening defined within a sidewall of the tube and disposed within the lumen of the sleeve.

15. The medical device of claim 10, further comprising:
a connecting member coupled to the sleeve and to the delivery member; and
a release mechanism configured to decouple the connecting member from the delivery member when activated.

* * * * *